United States Patent
Han et al.

(10) Patent No.: US 10,833,278 B2
(45) Date of Patent: Nov. 10, 2020

(54) COMPOUND AND ORGANIC LIGHT EMITTING DEVICE COMPRISING THE SAME

(71) Applicant: LG Chem, Ltd., Seoul (KR)

(72) Inventors: Mi Yeon Han, Daejeon (KR); Dong Hoon Lee, Daejeon (KR); Jung Oh Huh, Daejeon (KR); Boon Jae Jang, Daejeon (KR); Dong Uk Heo, Daejeon (KR); Min Woo Jung, Daejeon (KR)

(73) Assignee: LG Chem, Ltd. (KR)

( * ) Notice: Subject to any disclaimer, the term of this patent is extended or adjusted under 35 U.S.C. 154(b) by 276 days.

(21) Appl. No.: 15/775,517

(22) PCT Filed: Apr. 7, 2017

(86) PCT No.: PCT/KR2017/003835
§ 371 (c)(1),
(2) Date: May 11, 2018

(87) PCT Pub. No.: WO2017/213343
PCT Pub. Date: Dec. 14, 2017

(65) Prior Publication Data
US 2018/0351107 A1     Dec. 6, 2018

(30) Foreign Application Priority Data

Jun. 8, 2016 (KR) .................. 10-2016-0071222
Mar. 30, 2017 (KR) .................. 10-2017-0040550

(51) Int. Cl.
*H01L 51/00* (2006.01)
*H01L 51/50* (2006.01)
(Continued)

(52) U.S. Cl.
CPC ........ *H01L 51/0067* (2013.01); *C07D 251/24* (2013.01); *C07D 403/10* (2013.01);
(Continued)

(58) Field of Classification Search
CPC ............. H01L 51/5072; H01L 51/5012; H01L 51/5056; H01L 51/0052; H01L 51/5206;
(Continued)

(56) References Cited

U.S. PATENT DOCUMENTS 6,057,048 A    5/2000    Hu et al.
2011/0303907 A1    12/2011    Iwakuma et al.
(Continued)

FOREIGN PATENT DOCUMENTS

CN    102612518 A    7/2012
CN    103232843 A    8/2013
(Continued)

OTHER PUBLICATIONS

KR 10-2015-0115622 online machine translation as provided by KIPO, translated on Apr. 26, 2020.*
(Continued)

*Primary Examiner* — Golam Mowla
(74) *Attorney, Agent, or Firm* — Lerner, David, Littenberg, Krumholz & Mentlik, LLP

(57) ABSTRACT

The present invention relates to a novel heterocyclic compound and an organic light emitting device comprising the same.

8 Claims, 1 Drawing Sheet

(51) Int. Cl.
  *H01L 51/52* (2006.01)
  *C07D 251/24* (2006.01)
  *C09K 11/06* (2006.01)
  *C07D 471/04* (2006.01)
  *C07D 403/10* (2006.01)

(52) U.S. Cl.
  CPC ............ *C07D 471/04* (2013.01); *C09K 11/06* (2013.01); *H01L 51/0052* (2013.01); *H01L 51/0054* (2013.01); *H01L 51/0056* (2013.01); *H01L 51/0058* (2013.01); *H01L 51/0072* (2013.01); *H01L 51/5012* (2013.01); *H01L 51/5072* (2013.01); *H01L 51/5092* (2013.01); *H01L 51/5206* (2013.01); *H01L 51/5221* (2013.01); *H01L 51/5056* (2013.01); *H01L 51/5076* (2013.01)

(58) Field of Classification Search
  CPC ............ H01L 51/5221; H01L 51/5076; H01L 51/0056; H01L 51/0054; H01L 51/0058; H01L 51/5092; H01L 51/0067; H01L 51/0072
  See application file for complete search history.

(56) References Cited

U.S. PATENT DOCUMENTS

| | | |
|---|---|---|
| 2012/0232241 A1 | 9/2012 | Stoessel et al. |
| 2014/0251816 A1 | 9/2014 | Musselman et al. |
| 2014/0299192 A1 | 10/2014 | Lee et al. |
| 2016/0141514 A1 | 5/2016 | Lee et al. |
| 2016/0172598 A1 | 6/2016 | Lee et al. |
| 2016/0181548 A1 | 6/2016 | Parham et al. |
| 2017/0018718 A1 | 1/2017 | Jang et al. |
| 2018/0066180 A1 | 3/2018 | Huh et al. |

FOREIGN PATENT DOCUMENTS

| | | |
|---|---|---|
| CN | 104487432 A | 4/2015 |
| CN | 105308035 A | 2/2016 |
| CN | 105408448 A | 3/2016 |
| CN | 107431141 A | 12/2017 |
| EP | 2995616 A1 | 3/2016 |
| EP | 3287446 A2 | 2/2018 |
| EP | 3327008 A1 | 5/2018 |
| EP | 3327024 A1 | 5/2018 |
| EP | 3351536 A1 | 7/2018 |
| EP | 3351537 A1 | 7/2018 |
| JP | 4856882 B2 | 1/2012 |
| JP | 4907192 B2 | 3/2012 |
| KR | 20000051826 A | 8/2000 |
| KR | 20110117073 A | 10/2011 |
| KR | 20140094408 A | 7/2014 |
| KR | 20150002507 A | 1/2015 |
| KR | 101508424 B1 | 4/2015 |
| KR | 101529164 B1 | 6/2015 |
| KR | 20150115622 A | 10/2015 |
| KR | 20160026744 A | 3/2016 |
| KR | 20160034804 A | 3/2016 |
| KR | 20160045567 A | 4/2016 |
| KR | 20160141672 A | 12/2016 |
| WO | 2003012890 A2 | 2/2003 |
| WO | 2014209028 A1 | 12/2014 |
| WO | 2015014434 A1 | 2/2015 |
| WO | 2015152651 A1 | 10/2015 |
| WO | 2016052819 A1 | 4/2016 |
| WO | 2016171406 A2 | 10/2016 |

OTHER PUBLICATIONS

Extended European Search Report including Written Opinion for Application No. EP17810466.7 dated Oct. 25, 2018.
International Search Report for Application No. PCT/KR2017/003835 dated Jul. 31, 2017.
Search Report from Chinese Office Action for Application No. 2017800041624 dated Jul. 29, 2020; 3 pages.

* cited by examiner

[FIG. 1]
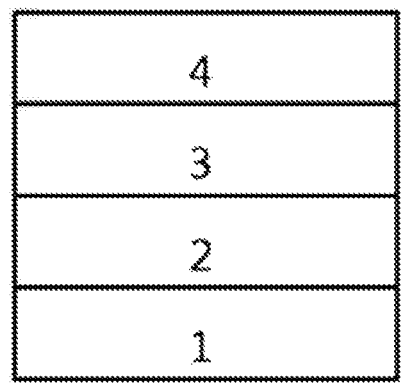
[FIG. 2]
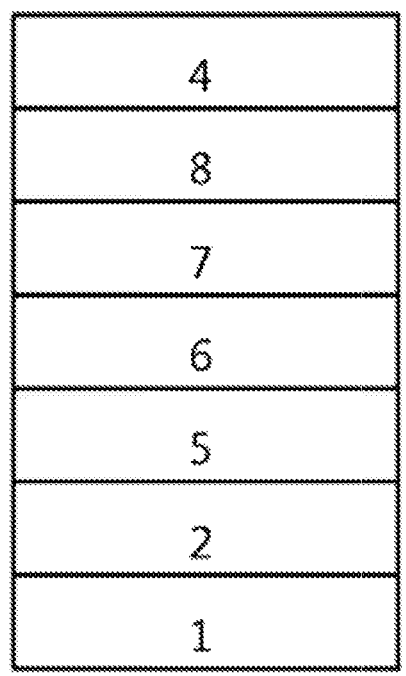

COMPOUND AND ORGANIC LIGHT EMITTING DEVICE COMPRISING THE SAME

CROSS-REFERENCE TO RELATED APPLICATION(S)

The present application is a national phase entry under 35 U.S.C. § 371 of International Application No. PCT/KR2017/003835, filed on Apr. 7, 2017, which claims the benefit of priority from Korean Patent Application No. 10-2016-0071222 filed on Jun. 8, 2016, and Korean Patent Application No. 10-2017-0040550, filed on Mar. 30, 2017, the disclosures of which are incorporated herein by reference.

TECHNICAL FIELD

The present invention relates to a novel triazine-based compound and an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode to the organic material layer, and when the injected holes and the electrons meet each other, an exciton is formed, and light is emitted when the exciton falls to a ground state again.

There is a continuing demand for developing a new material for organic materials used in such organic light emitting devices.

PRIOR ART LITERATURE

Patent Literature (Patent Literature 1) Korean Patent Publication No. 10-2000-0051826

DETAILED DESCRIPTION OF THE INVENTION

Technical Problem

It is one object of the present invention to provide a novel triazine-based compound and an organic light emitting device comprising the same.

Technical Solution

The present invention provides a compound represented by Chemical Formula 1 below:

[Chemical Formula 1]

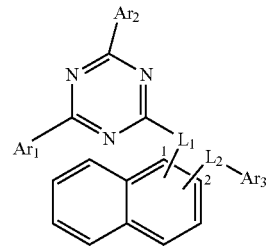

in Chemical Formula 1, $L_1$ and $L_2$ are bonded at positions 1 and 2 of naphthalene, or bonded at positions 2 and 1 of naphthalene, $L_1$ is a substituted or unsubstituted $C_{6-60}$ arylene; or a substituted or unsubstituted $C_{2-60}$ heteroarylene containing at least one of O, N, Si and S, $L_2$ is a bond; a substituted or unsubstituted $C_{6-60}$ arylene; or a substituted or unsubstituted $C_{2-60}$ heteroarylene containing at least one of O, N, Si and S, $Ar_1$ and $Ar_2$ are each independently a substituted or unsubstituted $C_{6-60}$ aryl; or a substituted or unsubstituted $C_{2-60}$ heteroaryl containing at least one of O, N, Si and S, and $Ar_3$ is a substituted or unsubstituted $C_{6-60}$ aryl; or a substituted or unsubstituted $C_{2-60}$ heteroaryl containing at least one of O, N, Si and S, with the proviso that $Ar_3$ does not have pyridine, quinoline, isoquinoline, phenanthridine, benzo[f]quinoline, benzo[f]isoquinoline, benzo[h]quinoline or benzo[h]isoquinoline structures.

In addition, the present invention provides an organic light emitting device comprising a first electrode; a second electrode provided to face the first electrode; and one or more organic material layers provided between the first electrode and the second electrode, wherein one or more of the organic materiel layers includes a compound represented by Chemical Formula 1.

Advantageous Effects

The compound represented by Chemical Formula 1 can be used as a material of an organic material layer of an organic light emitting device and can improve the efficiency, the low driving voltage and/or service life characteristics of the organic light emitting device. In particular, the compound represented by Chemical Formula 1 can be used as a hole injection, hole transport, hole injection and transport, light emission, electron transport, or electron injection material.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

DETAILED DESCRIPTION OF THE EMBODIMENTS

Hereinafter, the present invention will be described in more detail to help understanding of the present invention.

The present invention provides a compound represented by Chemical Formula 1.

In the present specification,

means a bond connected to another substituent group.

As used herein, the term "substituted or unsubstituted" means that substitution is performed by one or more substituent groups selected from the group consisting of deuterium; a halogen group; a nitrile group; a nitro group; a hydroxyl group; a carbonyl group; an ester group; an imide; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl groups; an aralkenyl group; an alkylaryl group; an alkylamine group; an aralkylamine group; a heteroarylamine group; an arylamine group; an arylphosphine group; or a heterocyclic group containing at least one of N, O, and S atoms, or there is no substituent group, or substitution is performed by a substituent group where two or more substituent groups of the exemplified substituent groups are connected or there is no substituent group. For example, the term "substituent group where two or more substituent groups are connected" may be a biphenyl group. That is, the biphenyl group may be an aryl group, or may be interpreted as a substituent group where two phenyl groups are connected.

In the present specification, the number of carbon atoms in a carbonyl group is not particularly limited, but is preferably 1 to 40 carbon atoms. Specifically, the carbonyl group may be a compound having the following structures, but is not limited thereto.

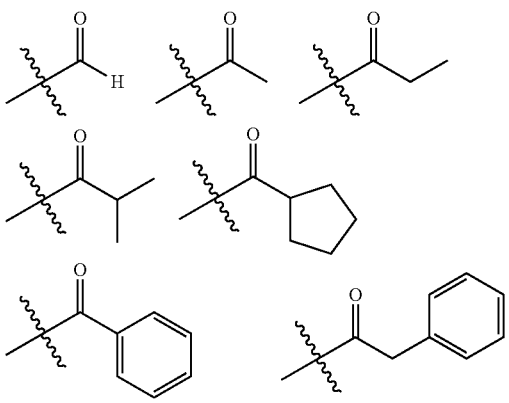

In the present specification, oxygen of an ester group may be substituted by a straight-chain, branched-chain, or cyclic alkyl group having 1 to 25 carbon atoms, or an aryl group having 6 to 25 carbon atoms. Specifically, the ester group may be compounds having the following structures, but is not limited thereto.

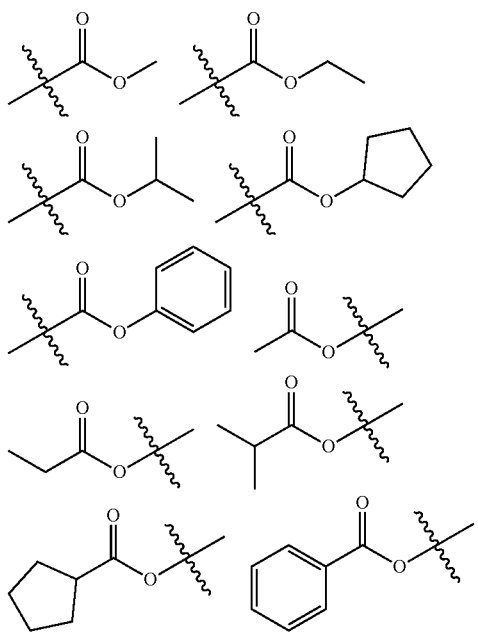

In the present specification, the number of carbon atoms in an imide group is not particularly limited but is preferably 1 to 25. Specifically, the imide group may be compounds having the following structures, but is not limited thereto.

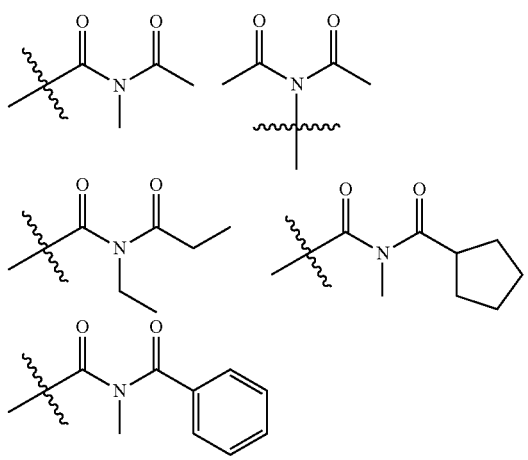

In the present specification, the silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, but is not limited thereto.

In the present specification, the boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, an alkyl group may be a straight chain or a branched chain, and the number of carbon atoms thereof is not particularly limited but is preferably 1 to 40. According to one embodiment, the alkyl group has 1 to 20 carbon atoms. According to another embodiment, the alkyl group has 1 to 10 carbon atoms. According to still another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, the alkenyl group may be a straight chain or a branched chain, and the number of carbon atoms thereof is not particularly limited but is preferably 2 to 40. According to one embodiment, the alkenyl group has 2 to 20 carbon atoms. According to another embodiment, the alkenyl group has 2 to 10 carbon atoms. According to still another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the cycloalkyl group has 3 to 30 carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the aryl group is not particularly limited, but preferably has 6 to 60 carbon atoms, and may be a monocyclic aryl group or a polycyclic aryl group. According to one embodiment, the aryl group has 6 to 30 carbon atoms. According to one embodiment, the aryl group has 6 to 20 carbon atoms. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group and a fluorenyl group or the like, but is not limited thereto.

In the present specification, a fluorenyl group may be substituted, and two substituent groups may be bonded to each other to form a spiro structure. In the case where the fluorenyl group is substituted,

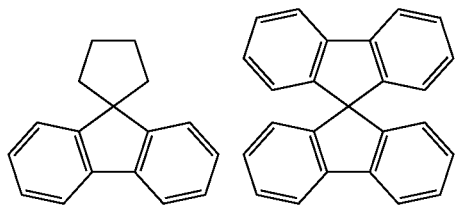

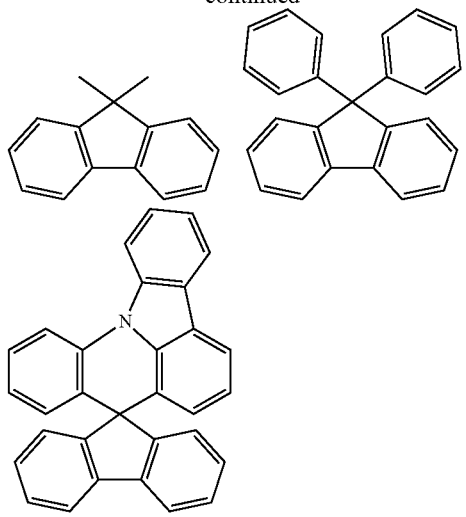

and the like can be formed. However, the structure is not limited thereto.

In the present specification, the heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamines can be applied to the aforementioned description of the heterocyclic group. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocycle is not a monovalent group but formed by combining two substituent groups.

In Chemical Formula 1, $L_1$ and $L_2$ are respectively bonded at positions 1 and 2 of naphthalene or bonded at positions 2 and 1 of naphthalene, and thereby can be represented by Chemical Formula 1-1 or 1-2 below:

[Chemical Formula 1-1]

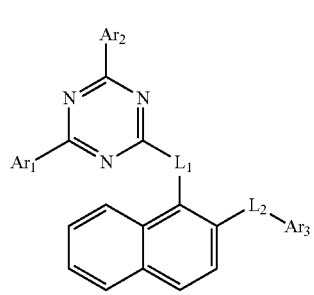

[Chemical Formula 1-2]

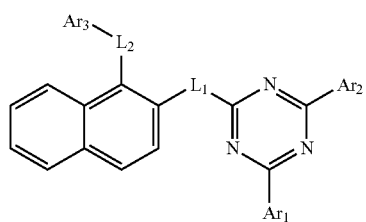

Preferably, $L_1$ is phenylene. More preferably, $L_1$ is 1,3-phenylene, or 1,4-phenylene.

Preferably, $L_2$ is a bond, or phenylene. More preferably, $L_2$ is a bond, 1,3-phenylene, or 1,4-phenylene.

Preferably, $Ar_1$ is phenyl.

Preferably, $Ar_2$ is phenyl, or biphenyl.

Preferably, $Ar_3$ is any one selected from the group consisting of:

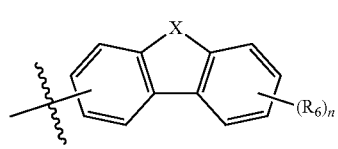

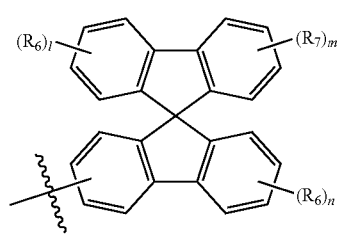

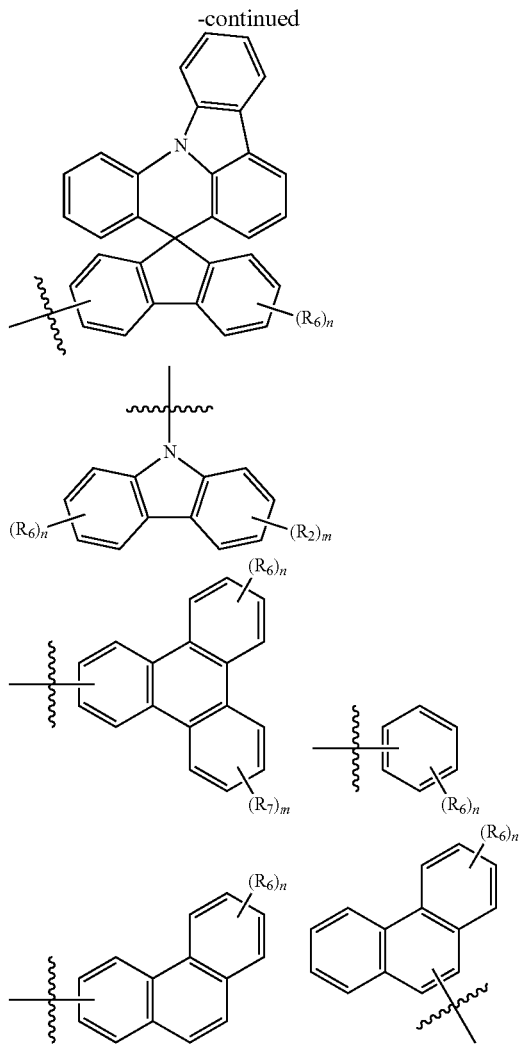

wherein,

X is $NR_1$, $CR_2R_3$, $SiR_4R_5$, S, or O, $R_1$ to $R_8$ are each independently hydrogen; deuterium; halogen; nitrile; nitro; amino; substituted or unsubstituted $C_{1-60}$ alkyl; substituted or unsubstituted $C_{3-60}$ cycloalkyl; substituted or unsubstituted $C_{2-60}$ alkenyl; substituted or unsubstituted $C_{6-60}$ aryl; or substituted or unsubstituted $C_{2-60}$ heterocyclic group containing one or more of O, N, Si and S, n, m and l are each independently an integer of 0 to 4.

More preferably, $Ar_3$ is any one selected from the group consisting of:

(a)

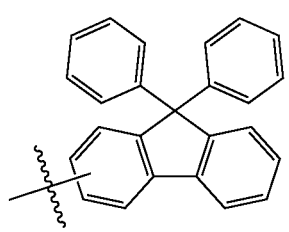

-continued
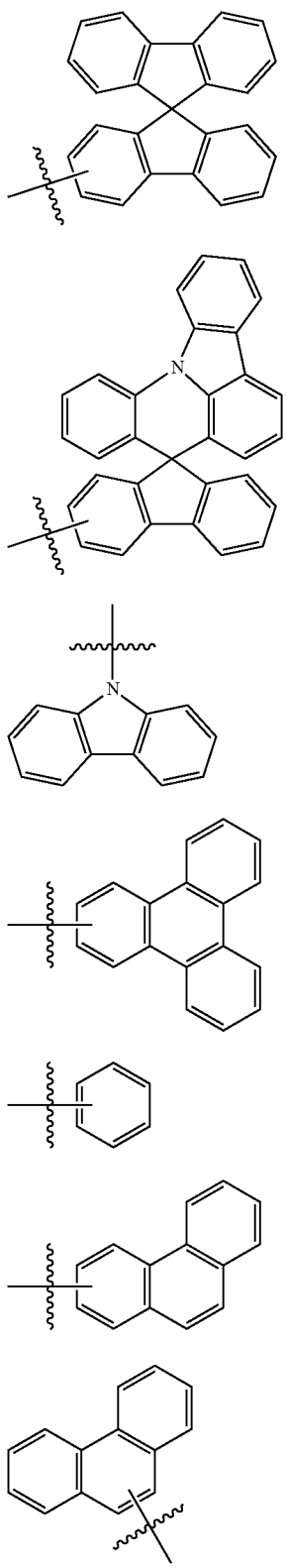
More preferably, $Ar_3$ is the (a), (b), or (c), and $L_2$ is a bond; $Ar_3$ is the (d), (f), (g), or (h), and $L_2$ is 1,4-phenylene; or $Ar_3$ is the (e), and $L_2$ is a bond, 1,3-phenylene, or 1,4-phenylene.
The compound represented by Chemical Formula 1 may be selected from the group consisting of the following compounds.
1
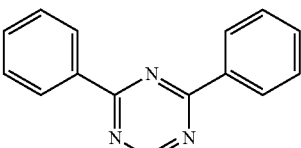
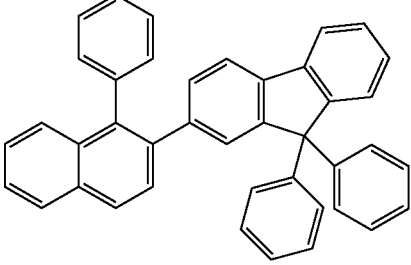
2
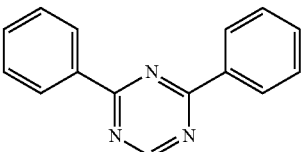
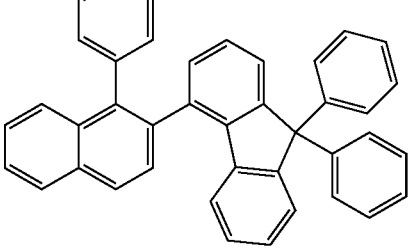
3
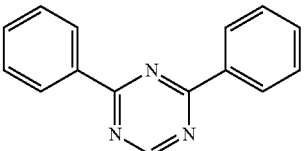
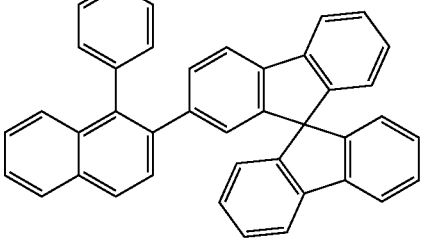

4
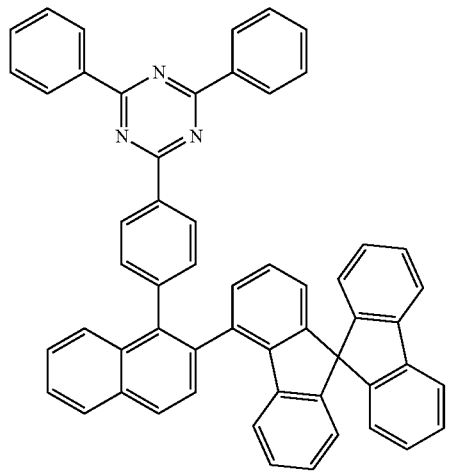
5
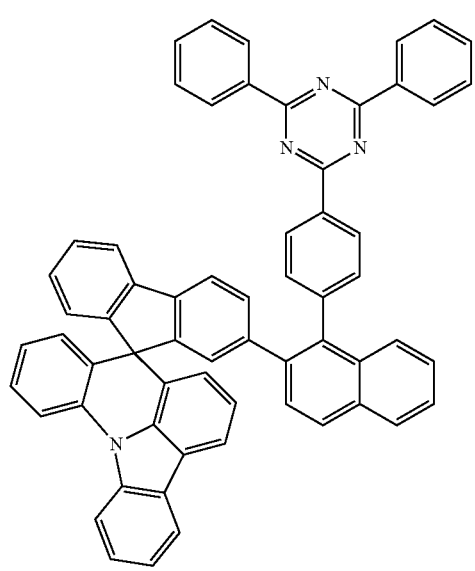
6
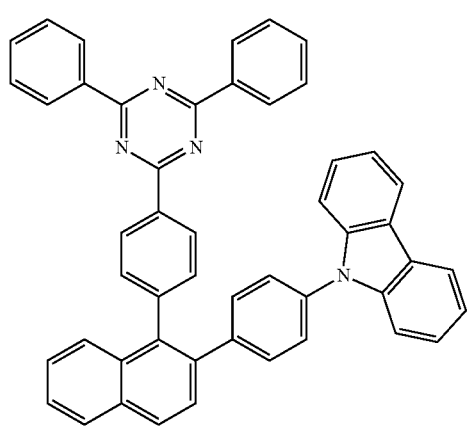
7
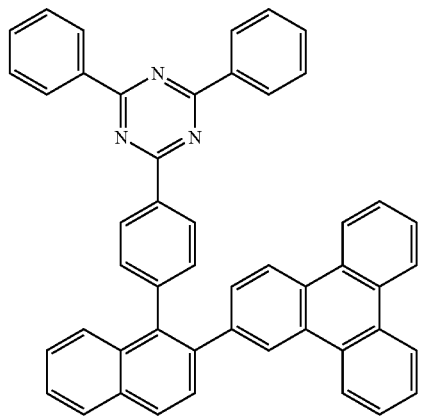
8
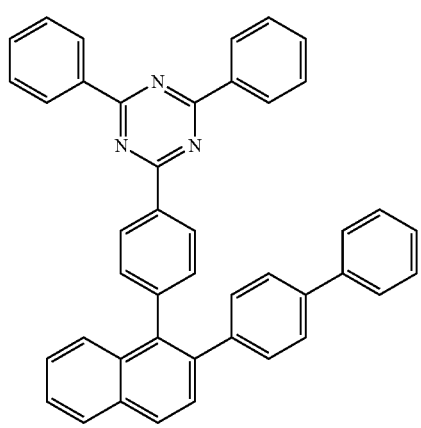
9
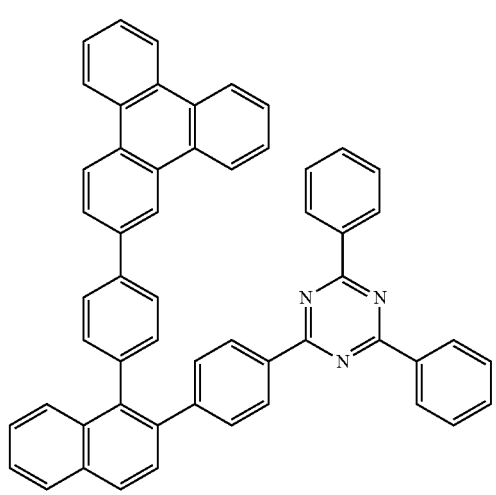

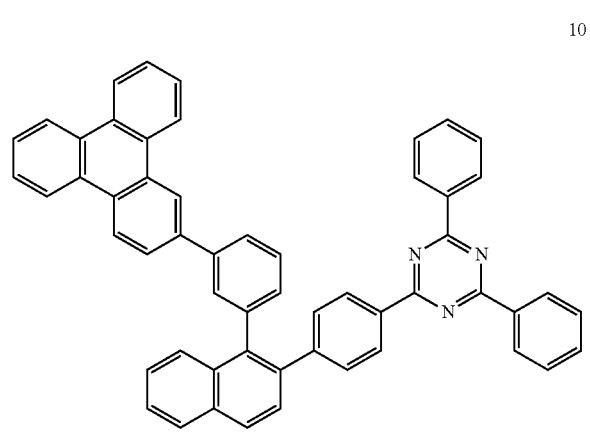
10
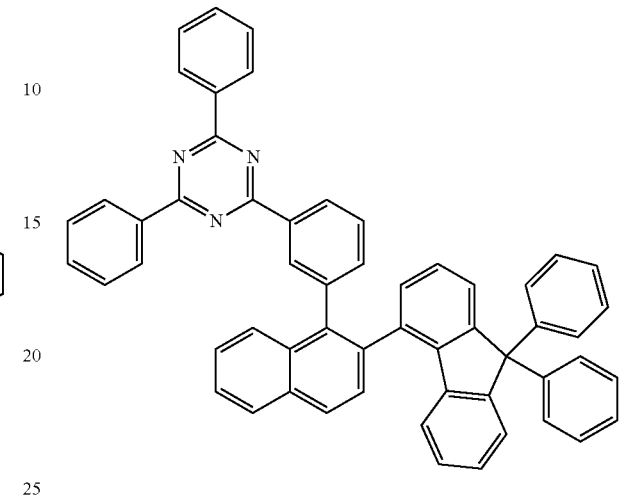
5
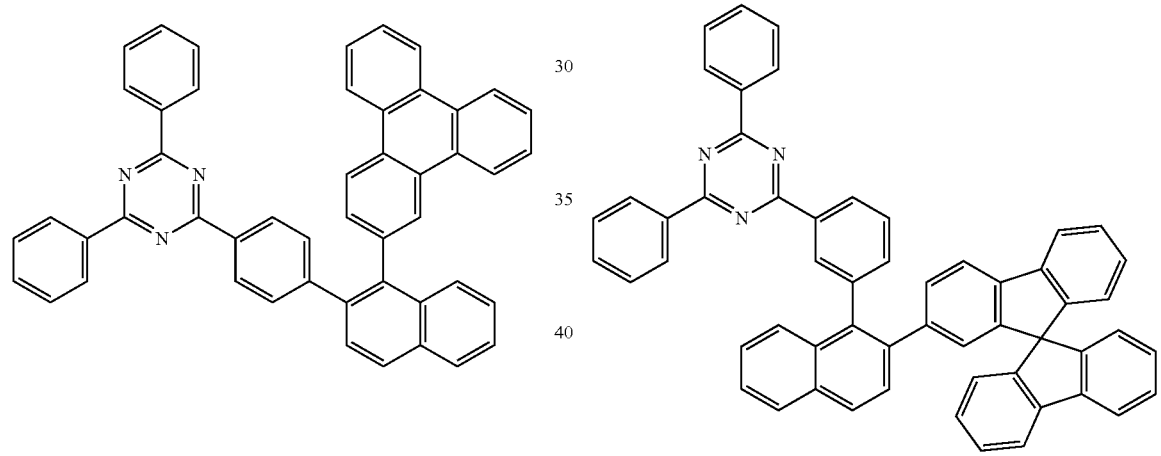
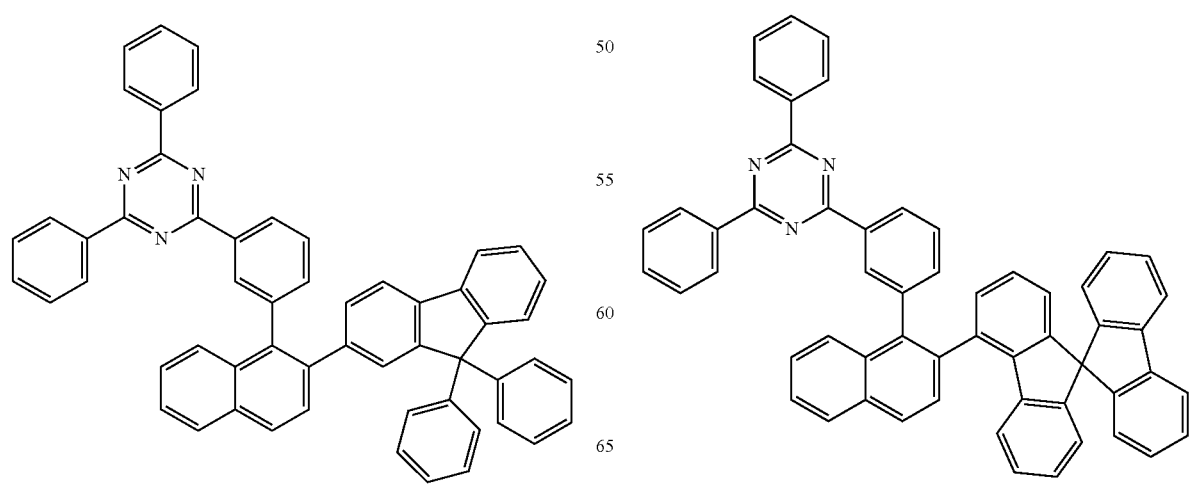

16
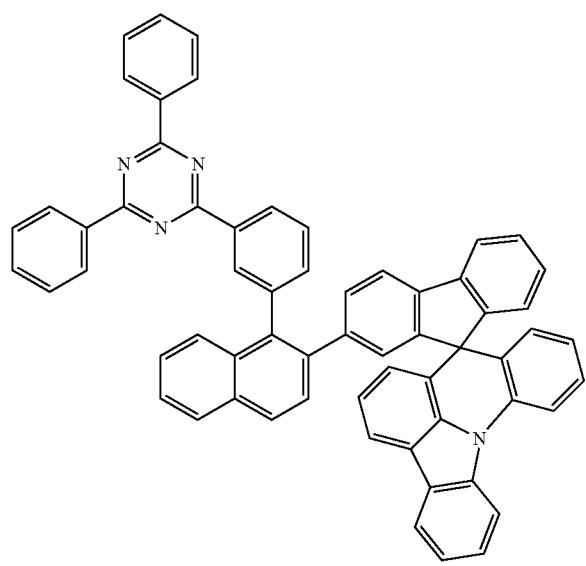
17
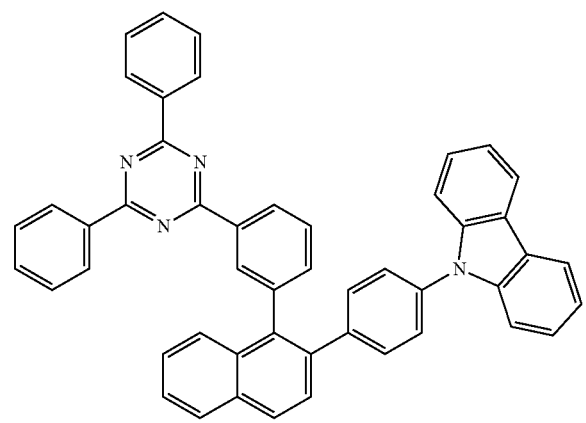
18
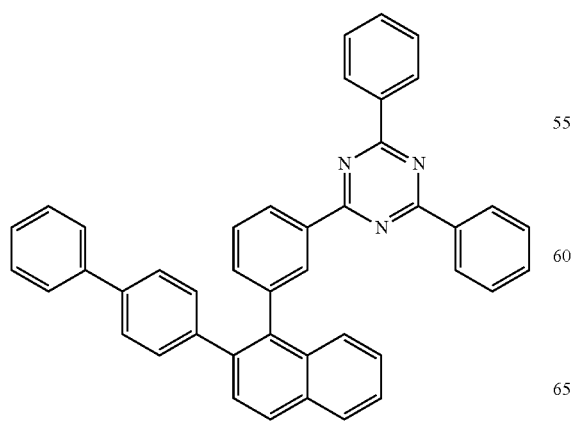
19
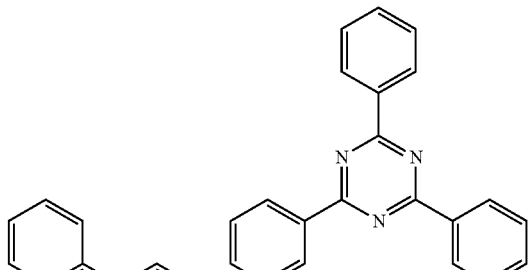
20
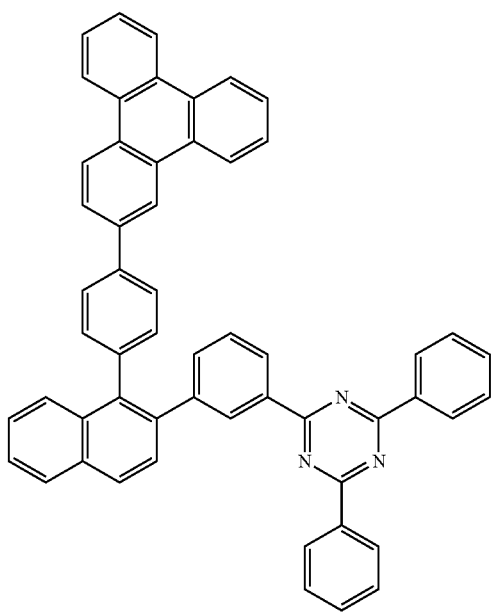
21
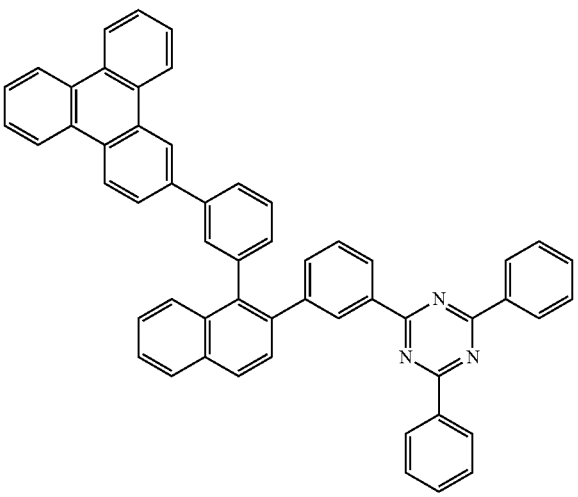

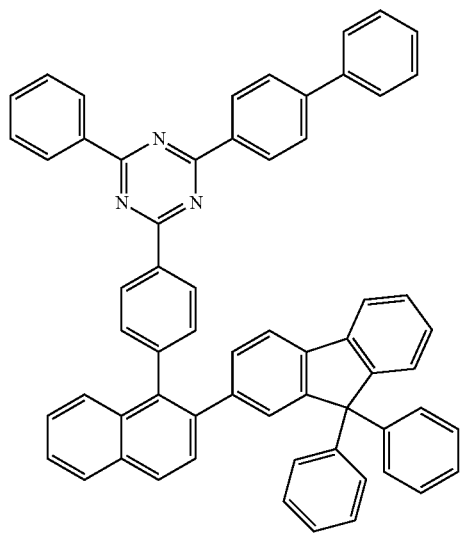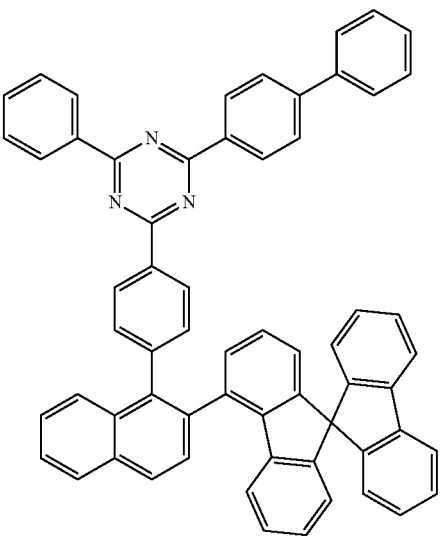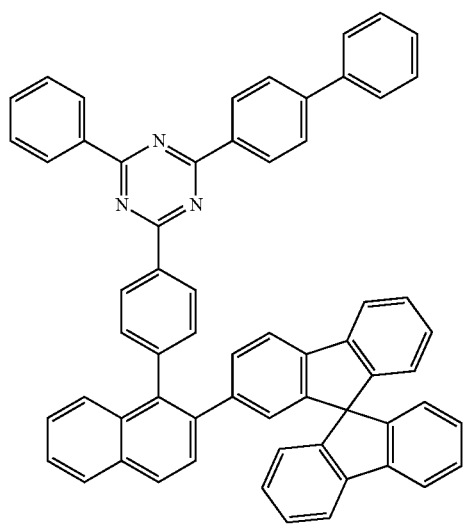

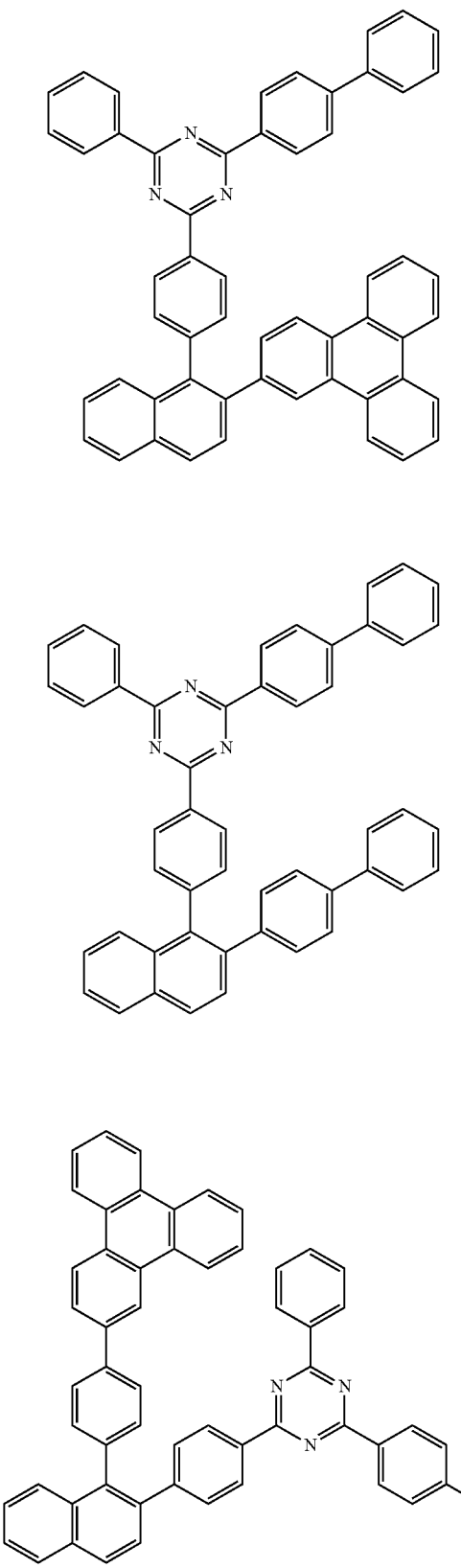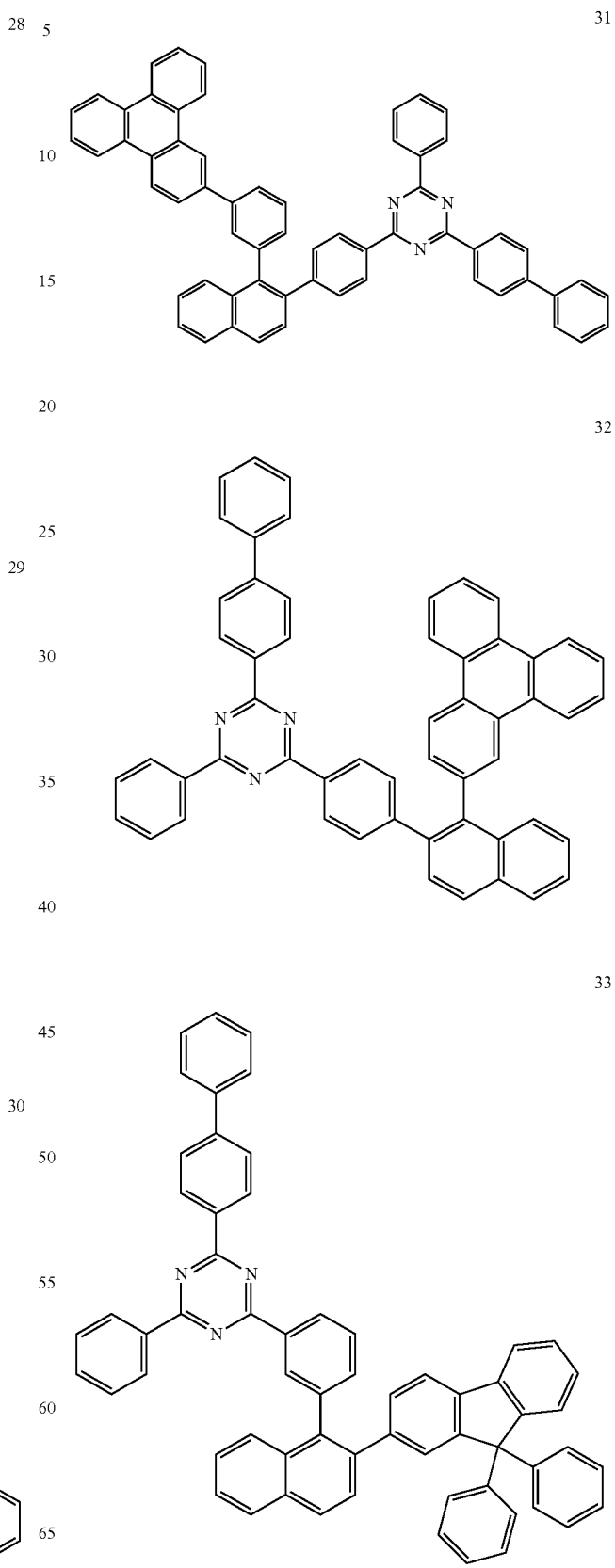

34
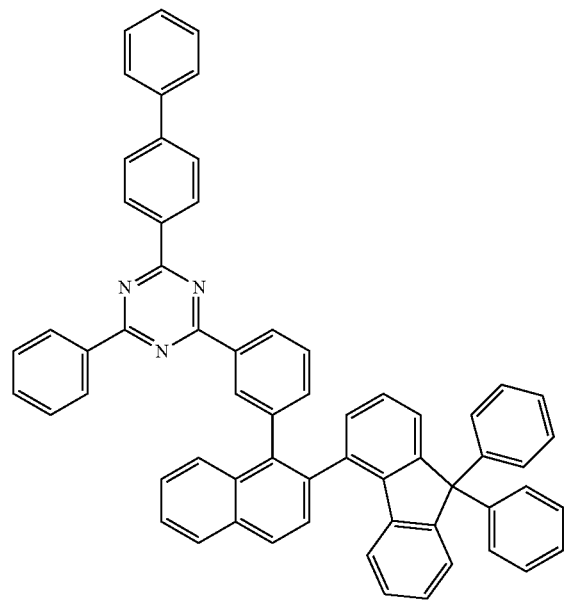
35
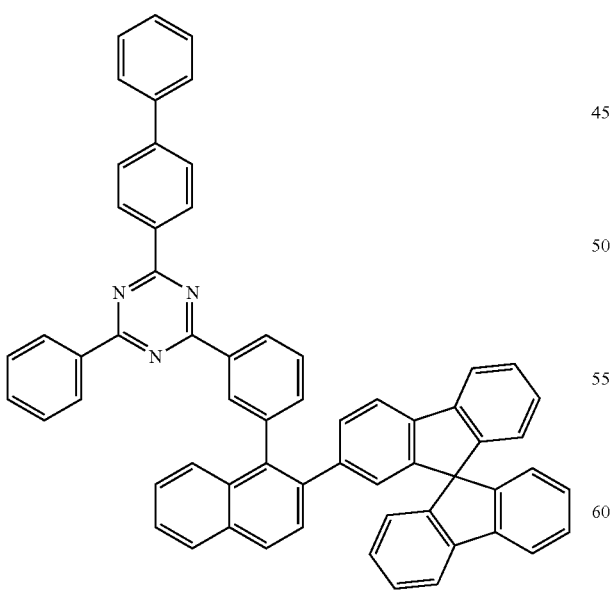
36
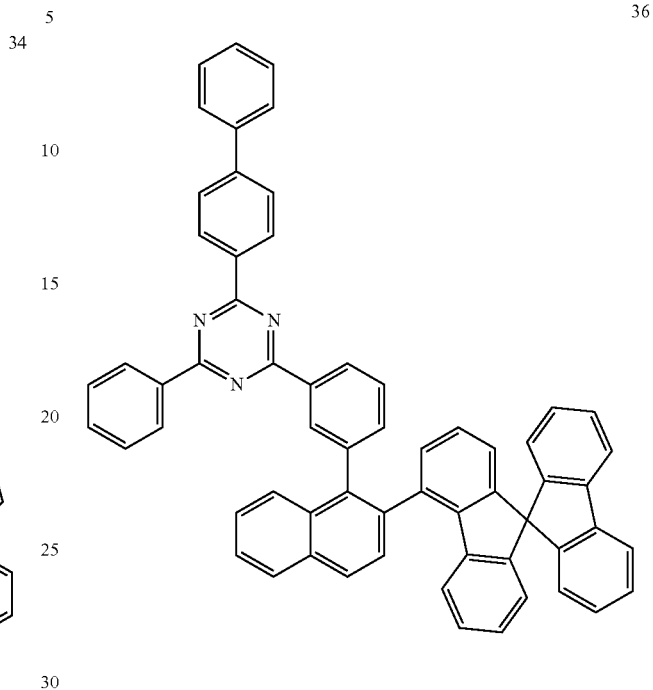
37
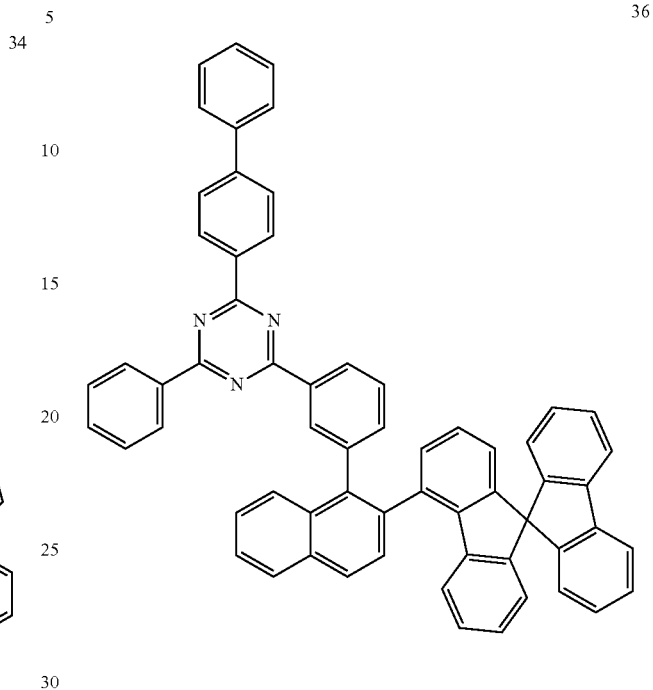

38
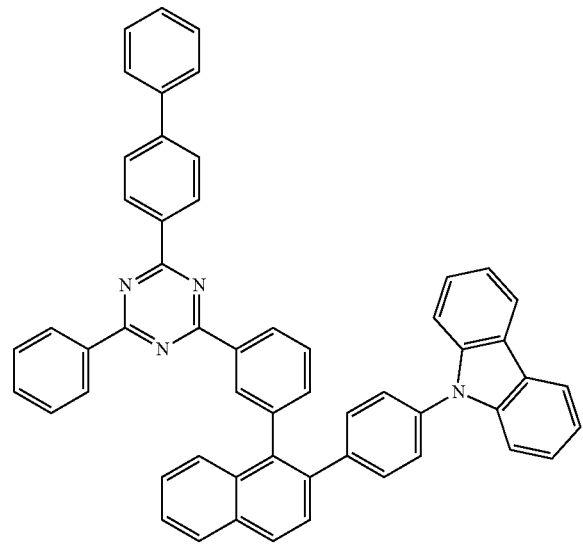
39
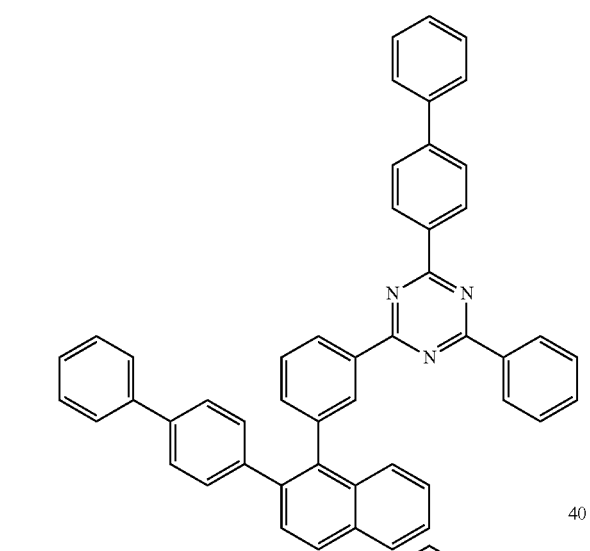
40
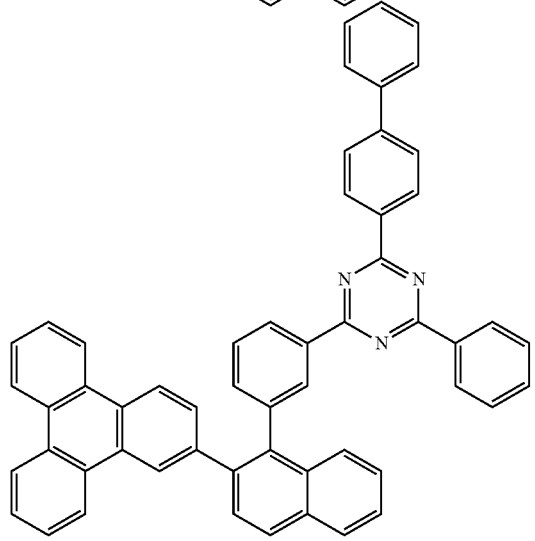
41
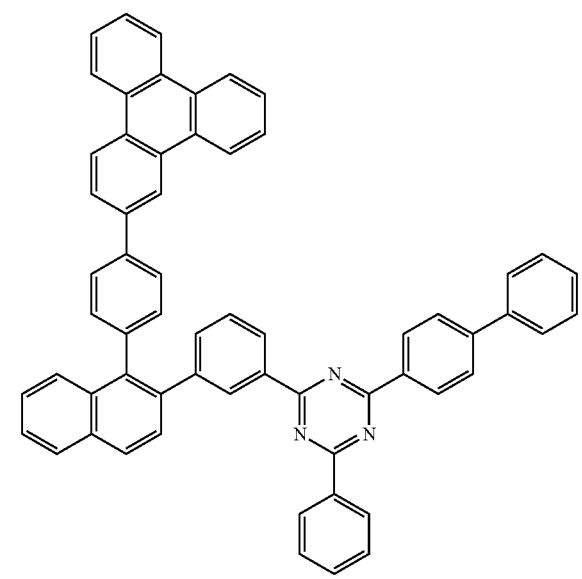
42
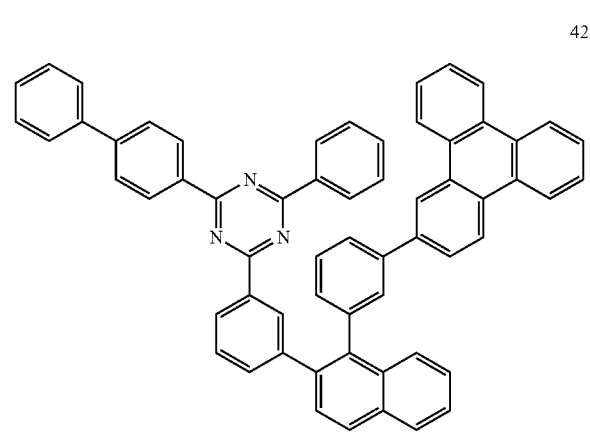
43
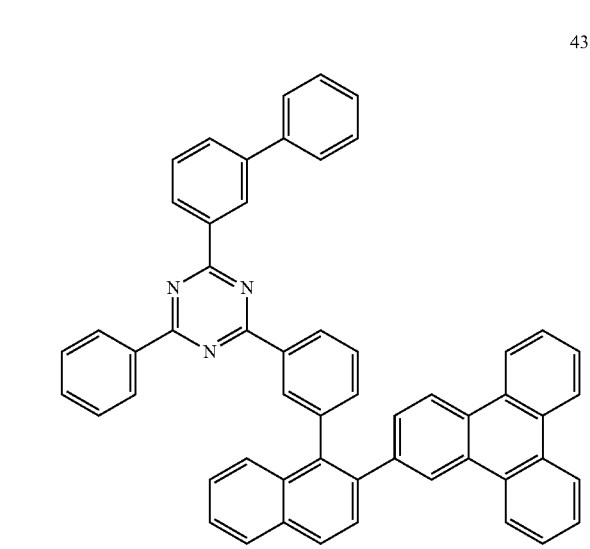

44
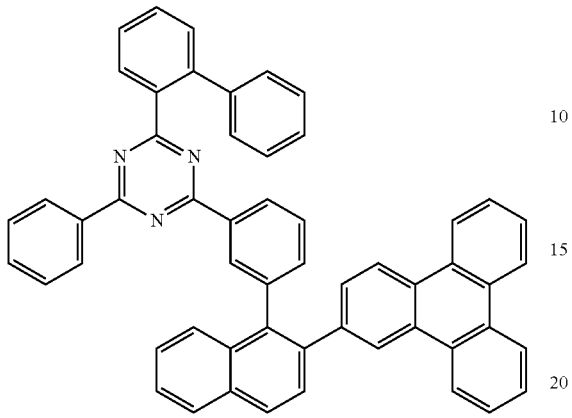
45
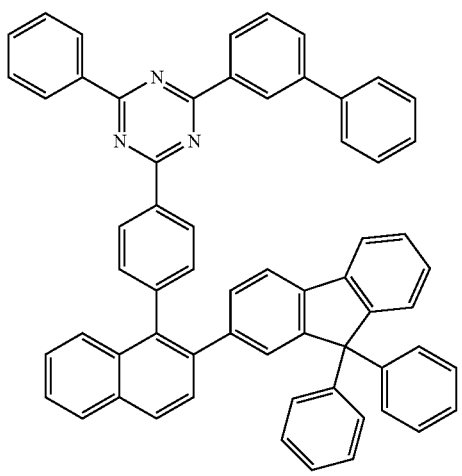
46
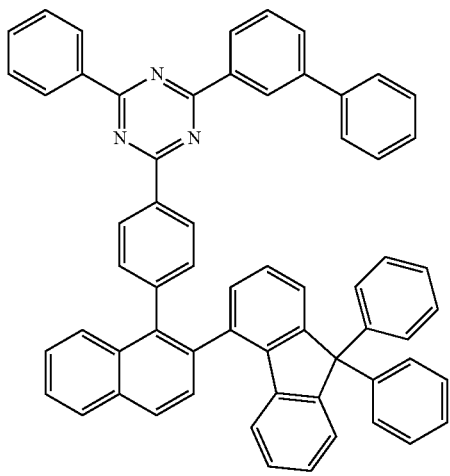
47
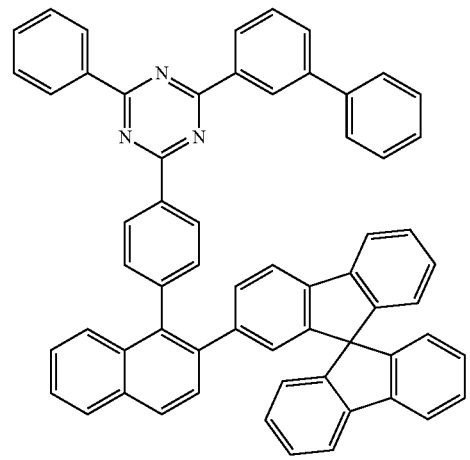
48
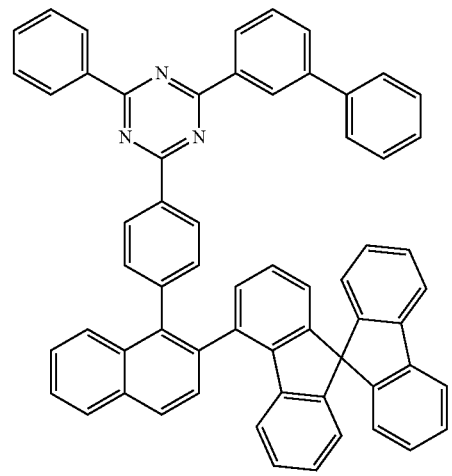
49
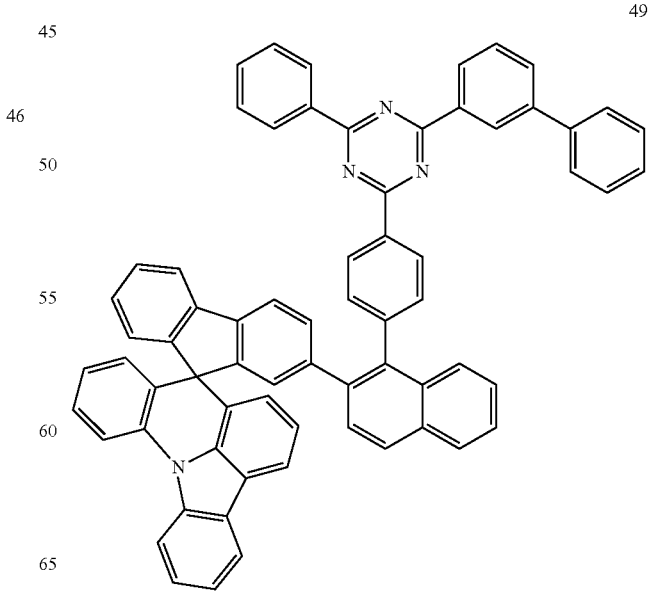

50
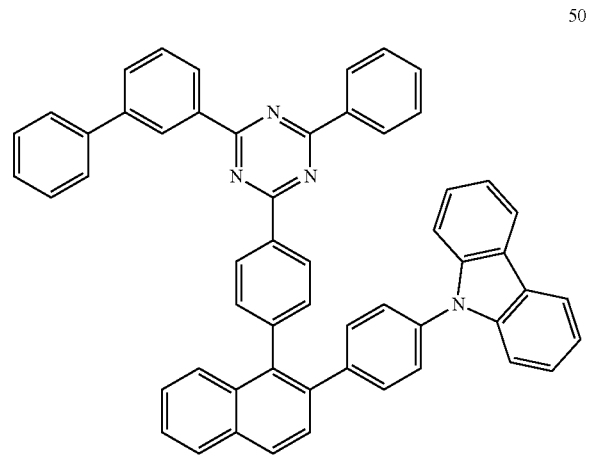
51
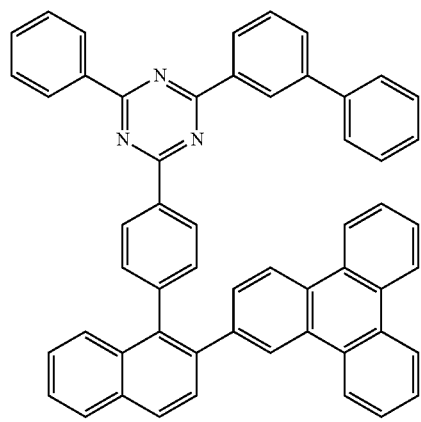
52
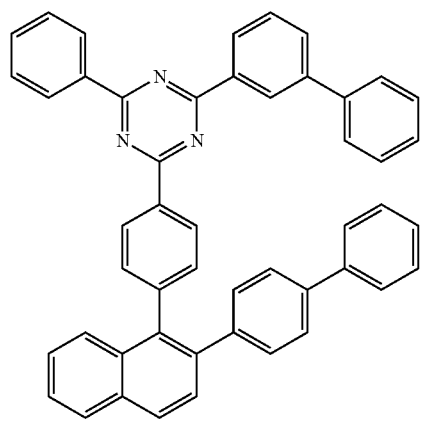
53
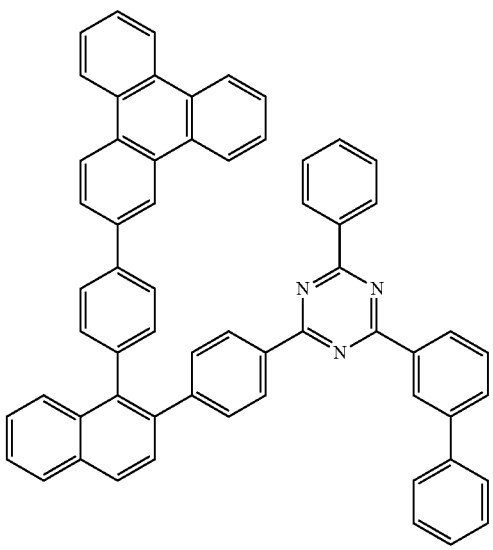
54
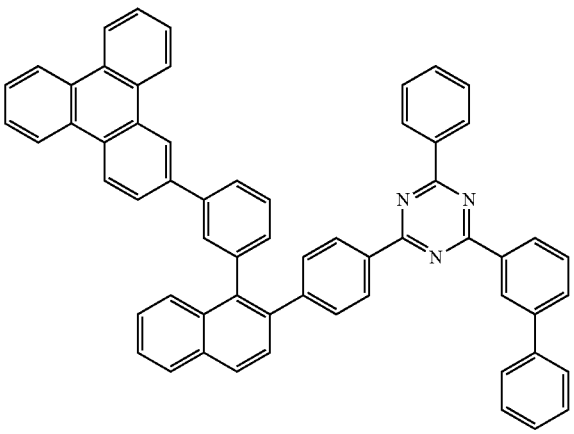
55
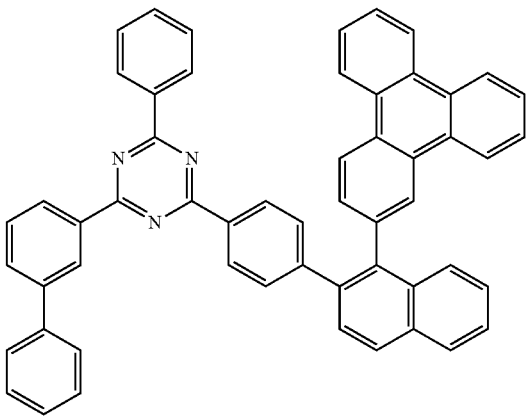

56
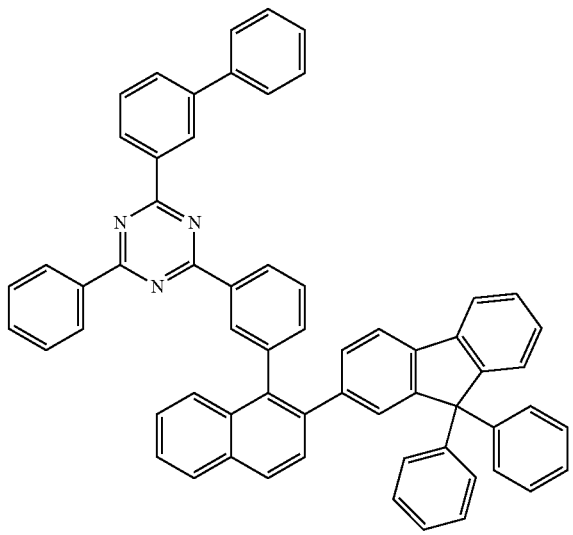
57
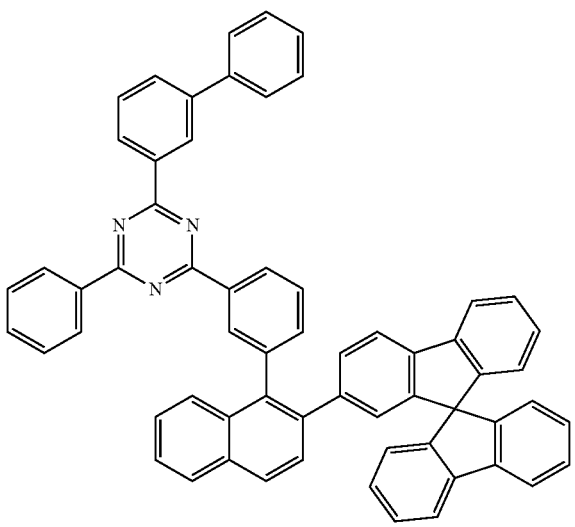
59
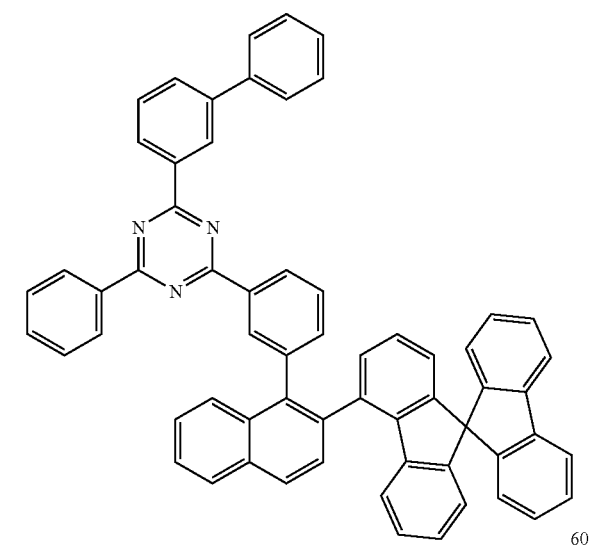
60
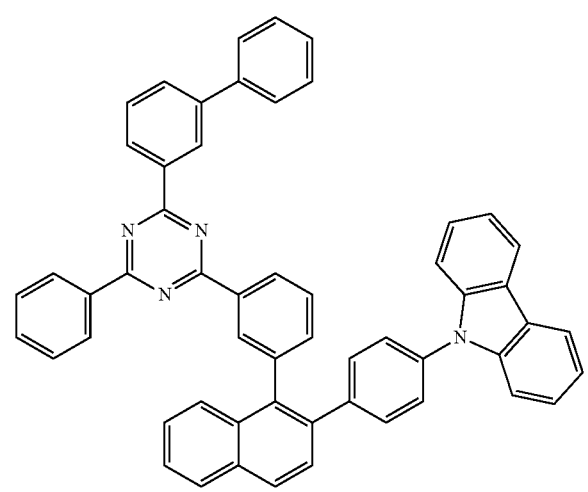

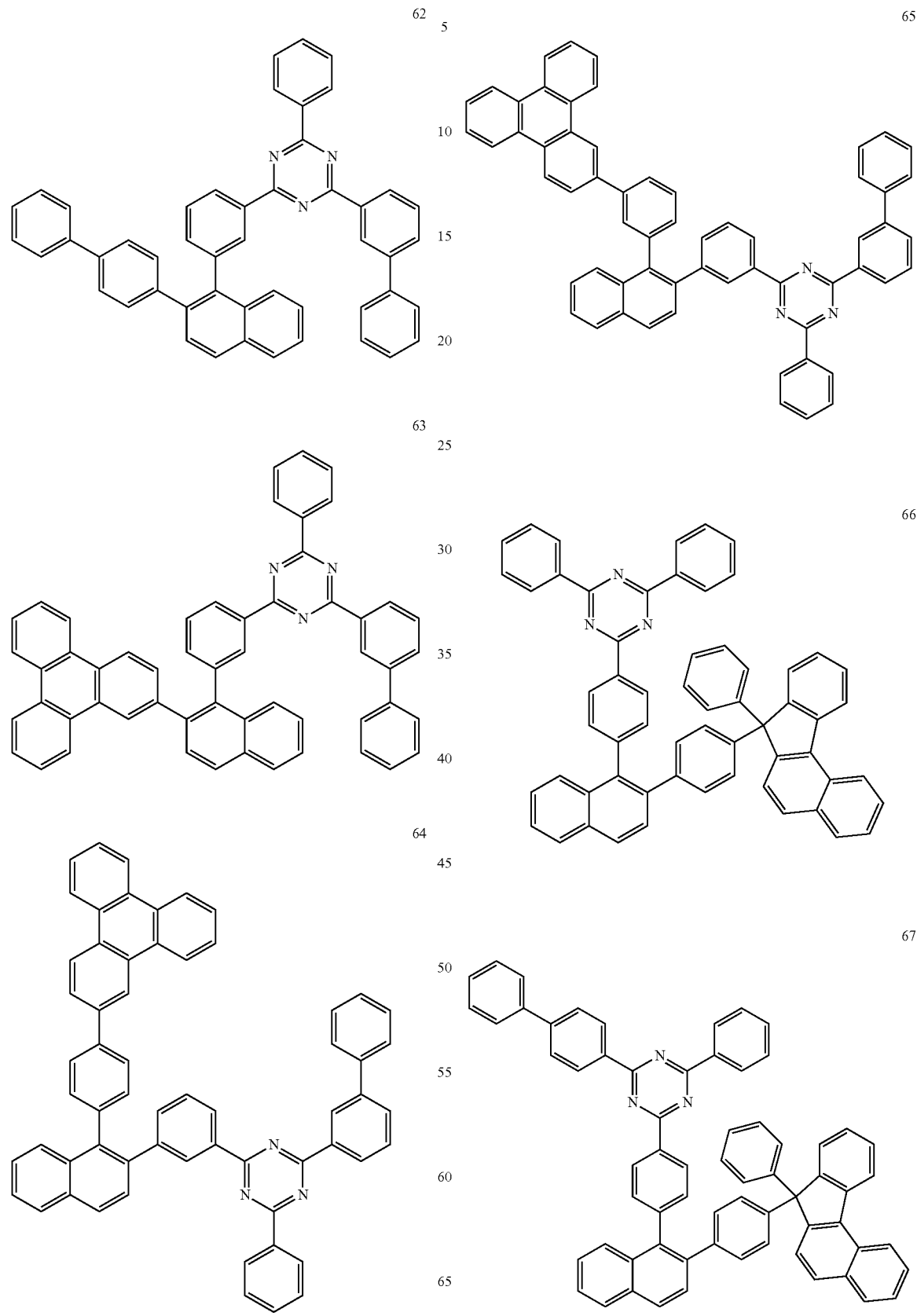

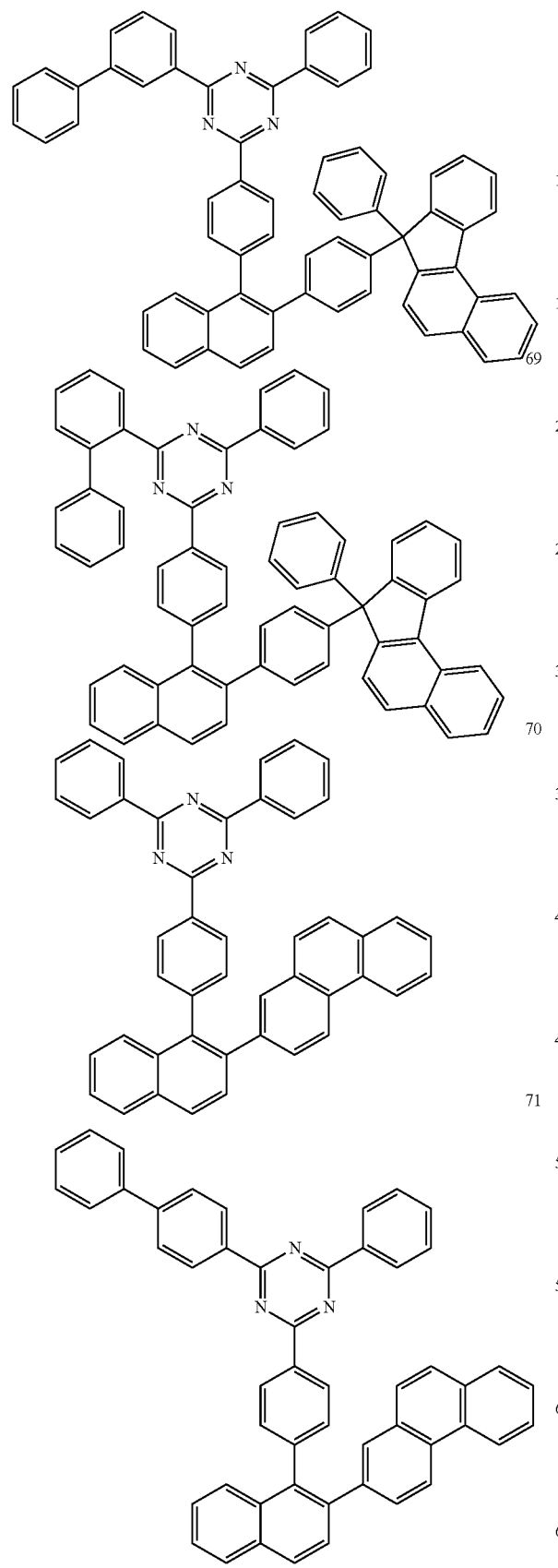
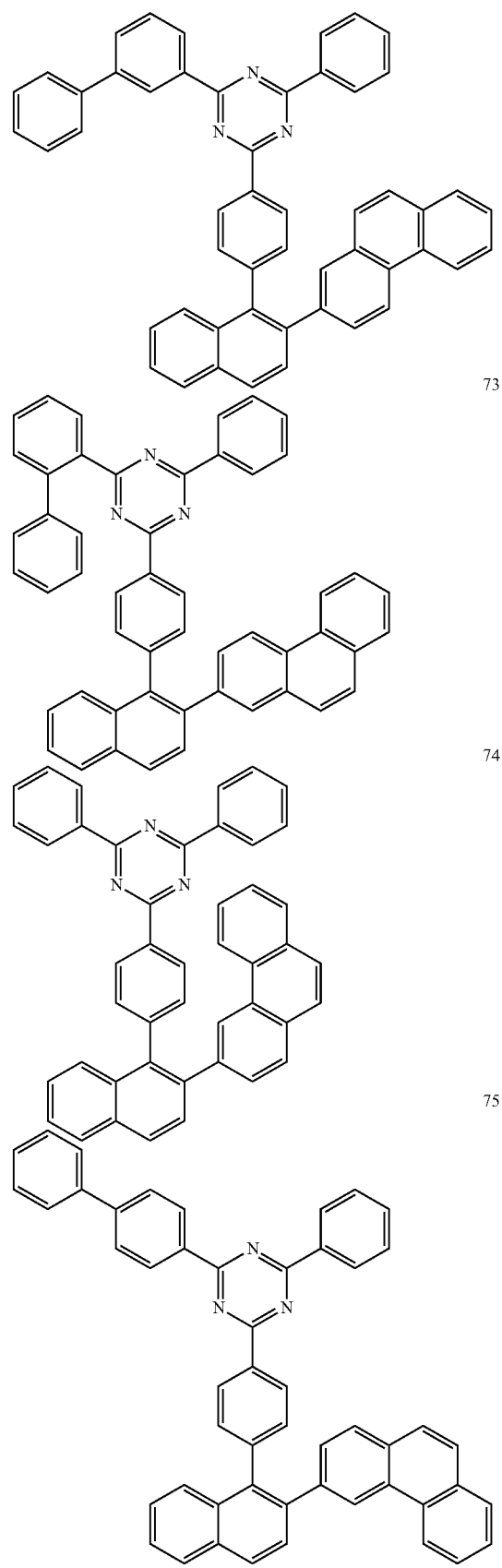

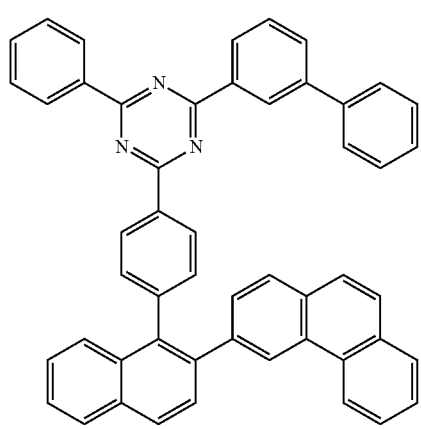
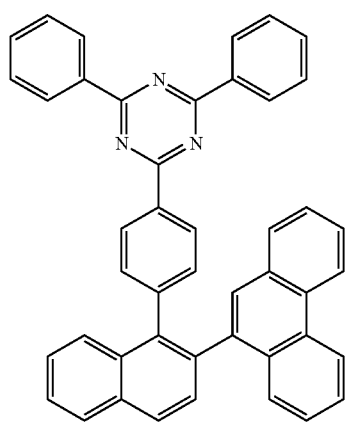
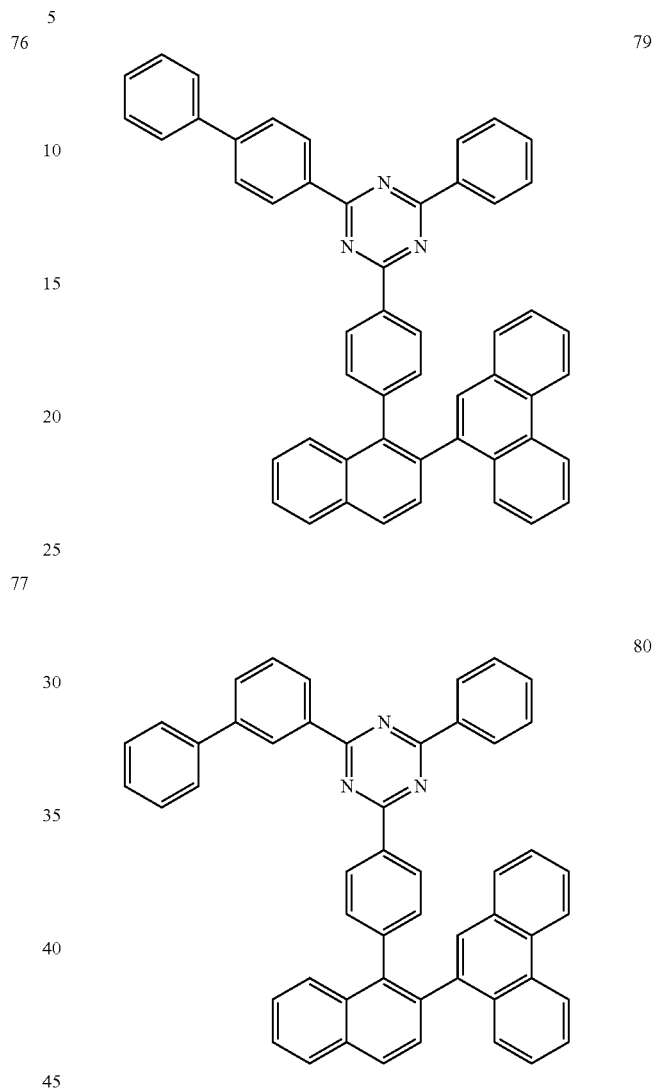
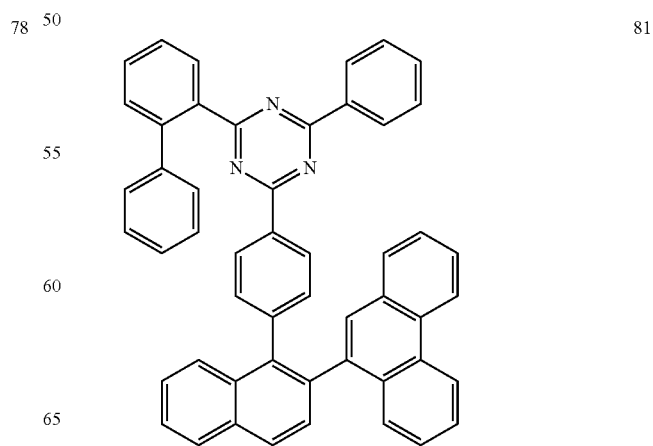

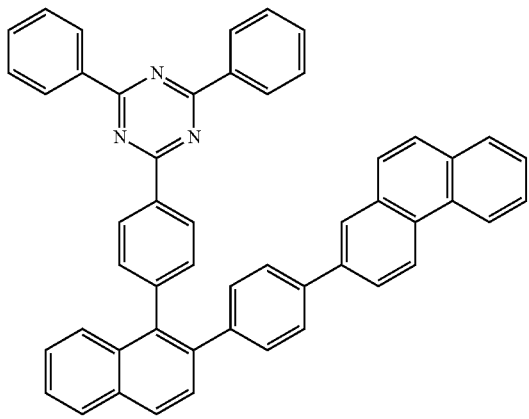

82

The compound represented by Chemical Formula 1 can be prepared as in Reaction Scheme 1 below:

[Reaction Scheme 1]

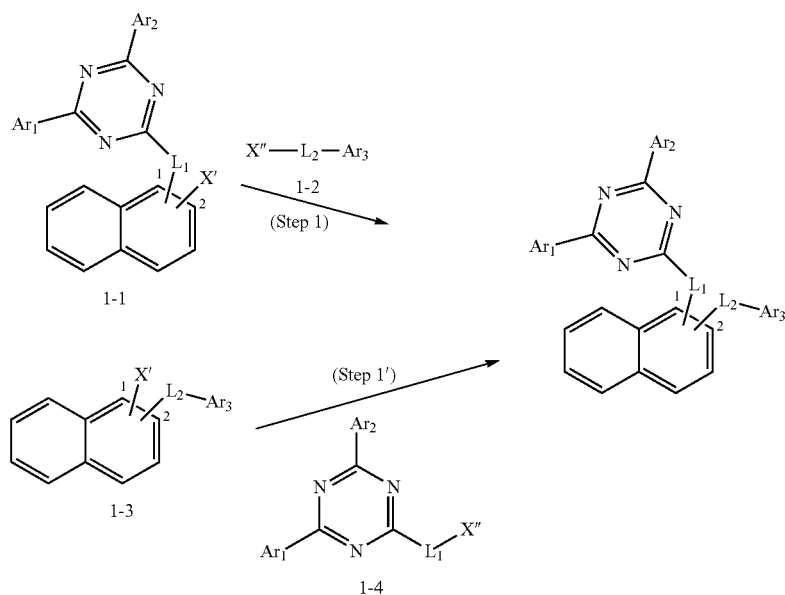

In Reaction Scheme 1, $L_1$, $L_2$, $Ar_1$, $Ar_2$ and $Ar_3$ are as defined above, and X' and X" mean a substituent group used in the Suzuki coupling reaction. In addition, the step 1 or the step 1' means a Suzuki coupling reaction, and the preparation method can be further specified in the preparation example described later.

Further, the present invention provides an organic light emitting device comprising the compound represented by Chemical Formula 1. In one example, the present invention provides an organic light emitting device including: a first electrode; a second electrode provided to face the first electrode; and one or more organic material layers provided between the first electrode and the second electrode, wherein one or more of the organic material layers include the compound of Chemical Formula 1.

The organic material layer of the organic light emitting device of the present invention may have a single layer structure, or a multilayered structure in which two or more organic material layers are laminated. For example, the organic light emitting device of the present invention may have a structure including a hole injection layer, a hole transport layer, a light emitting layer, an electron transport layer, an electron injection layer, and the like as the organic material layer. However, the structure of the organic light emitting device is not limited thereto, but may include a smaller number of organic layers.

Moreover, the organic material layer may include a hole injection layer, a hole transport layer, or a layer that injects and transports holes simultaneously, and the hole injection layer, the hole transport layer, or the layer that injects and transports holes simultaneously include the compound represented by Chemical Formula 1.

Further, the organic material layer may include a light emitting layer, and the light emitting layer includes the compound represented by Chemical Formula 1.

In addition, the organic material layer may include an electron transport layer or an electron injection layer, and the electron transport layer or the electron injection layer includes the compound represented by Chemical Formula 1.

Further, the electron transport layer, the electron injection layer, or a layer simultaneously performing electron transporting and electron injection comprises the compound represented by Chemical Formula 1.

Further, the organic material layer includes a light emitting layer and an electron transport layer, and the electron transport layer comprises the compound represented by Chemical Formula 1.

Further, the organic light emitting device according to the present invention may be an organic light emitting device having a structure (normal type) where an anode, one or more organic material layers, and a cathode are sequentially laminated on a substrate. Further, the organic light emitting device according to the present invention may be an organic light emitting device having an inverted direction structure (inverted type) where the cathode, one or more organic material layers, and the anode are sequentially laminated on the substrate. For example, the structure of the organic light emitting device according to the present invention is illustrated in FIGS. 1 and 2.

FIG. 1 illustrates an example of an organic light emitting device including a substrate 1, an anode 2, a light emitting layer 3, and a cathode 4. In such a structure, the compound represented by Chemical Formula 1 may be included in the light emitting layer.

FIG. 2 illustrates an example of an organic light emitting device including a substrate 1, an anode 2, a hole injection layer 5, a hole transport layer 6, a light emitting layer 7, an electron transport layer 8, and a cathode 4. In such a structure, the compound represented by Chemical Formula 1 may be included in one or more layers of the hole injection layer, the hole transport layer, the light emitting layer, and the electron transport layer.

The organic light emitting device according to the present invention may be manufactured by using materials and methods known in the art, except that one or more of organic material layers include the compound represented by Chemical Formula 1. Further, in the case where the organic light emitting device includes a plurality of organic material layers, the organic material layers may be formed of the same materials or different materials.

For example, the organic light emitting device according to the present invention may be manufactured by sequentially laminating the first electrode, the organic material layer, and the second electrode on the substrate. In this case, the organic light emitting device may be manufactured by depositing a metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, the organic material layer, and an anode material on the substrate.

Further, the compound represented by Chemical Formula 1 may be formed as the organic material layer by a vacuum deposition method as well as a solution coating method during the production of the organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

In one example, the first electrode is the anode, and the second electrode is the cathode, and alternatively, the first electrode is the cathode, and the second electrode is the anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or SnO$_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or LiO$_2$/Al, and the like, but are not limited thereto.

The hole injection layer is a layer injecting the holes from the electrode, and the hole injection material is preferably a compound which has an ability of transporting the holes, a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrile hexaazatriphenylene-based organic material, a quinacridone-based organic material, a perylene-based organic material, anthraquinone, polyaniline and polythiophene-based conductive polymer, and the like, but are not limited thereto.

The hole transport layer is a layer receiving the holes from the hole injection layer and transporting the holes to the light emitting layer, and the hole transport material is a material that can receive the holes from the anode or the hole injection layer and transport the holes to the light emitting layer, and a material having large mobility to the holes is suitable. Specific examples thereof include an arylamine-based organic material, a conductive polymer, a block copolymer in which a conjugate portion and a non-conjugate portion are present together, and the like, but are not limited thereto.

The light emitting material is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex (Alq$_3$); a carbazole-based compound; a dimerized styryl compound; BAlq; a 10-hydroxybenzoquinoline-metal compound; benzoxazole, benzothiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic cycle derivative, a heterocycle-containing compound, or the like. Specific examples of the condensed aromatic cycle derivative include an anthracene derivative, a pyrene derivative, a naphthalene derivative, a pentacene derivative, a phenanthrene compound, a fluoranthene compound, and the like, and specific examples of the heterocycle-containing compound include a carbazole derivative, a dibenzofuran derivative, a ladder-type furan compound, a pyrimidine derivative, and the like, but are not limited thereto.

Examples of the dopant material include an aromatic amine derivative, a styrylamine compound, a boron complex, a fluoranthene compound, a metal complex, and the like. Specifically, the aromatic amine derivative is a condensed aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including Alq$_3$; an organic radical compound; a hydroxyflavone-metal complex, and the like, but are not limited thereto. Particularly, it is preferable to use the compound represented by Chemical Formula 1 as an electron transport material. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

Further, the compound represented by Chemical Formula 1 may be included in an organic solar cell or an organic transistor in addition to the organic light emitting device.

The preparation of the above-described organic light emitting device of the present invention will be described in detail in the following examples. However, these examples are presented for illustrative purposes only, and the scope of the present invention is not limited thereto.

PREPARATION EXAMPLES

Preparation Example 1: Preparation of Compound 1

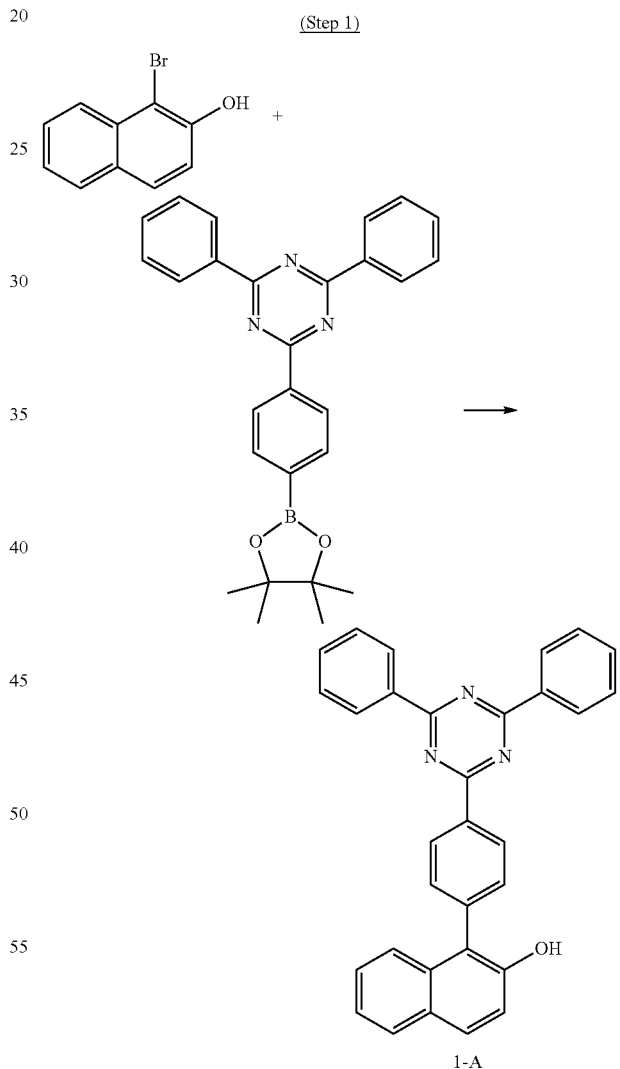

1-Bromonaphthalen-2-ol (20.0 g, 89.7 mmol), 2,4-diphenyl-6-(4-(4,4,5,5-tetramethyl-1,3,2-dioxaborolan-2-yl)phenyl)-1,3,5-triazine (50.0 g, 94.1 mmol) and potassium carbonate (24.8 g, 179.3 mmol) were added, and the mixture was heated and stirred. After refluxing, tetrakis(triphenylphosphine)palladium(0) (1.2 g, 1.0 mmol) was added thereto and the mixture was heated and stirred for further 5 hours. After completion of the reaction, the temperature was lowered to room temperature, and then the impurities were mainly removed by filtration. The filtrate was added in water and extracted with chloroform to obtain an organic layer, which was then dried over anhydrous magnesium sulfate. After distillation under reduced pressure, it was washed with ethanol to prepare compound 1-A (39 g, yield 96%).

MS: [M+H]⁺=452

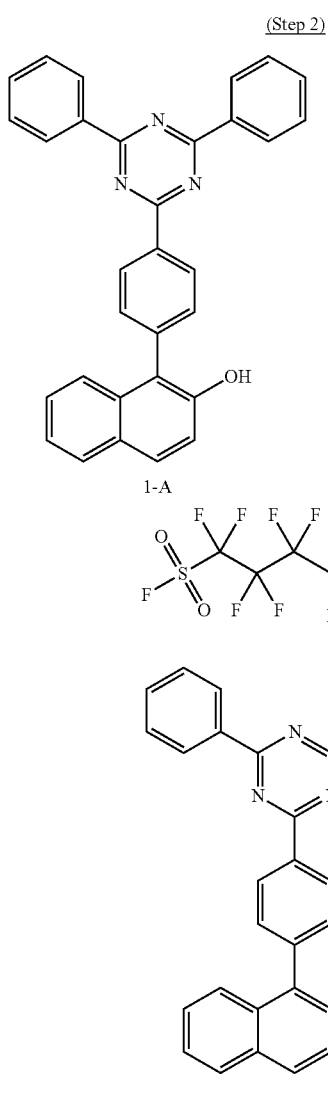

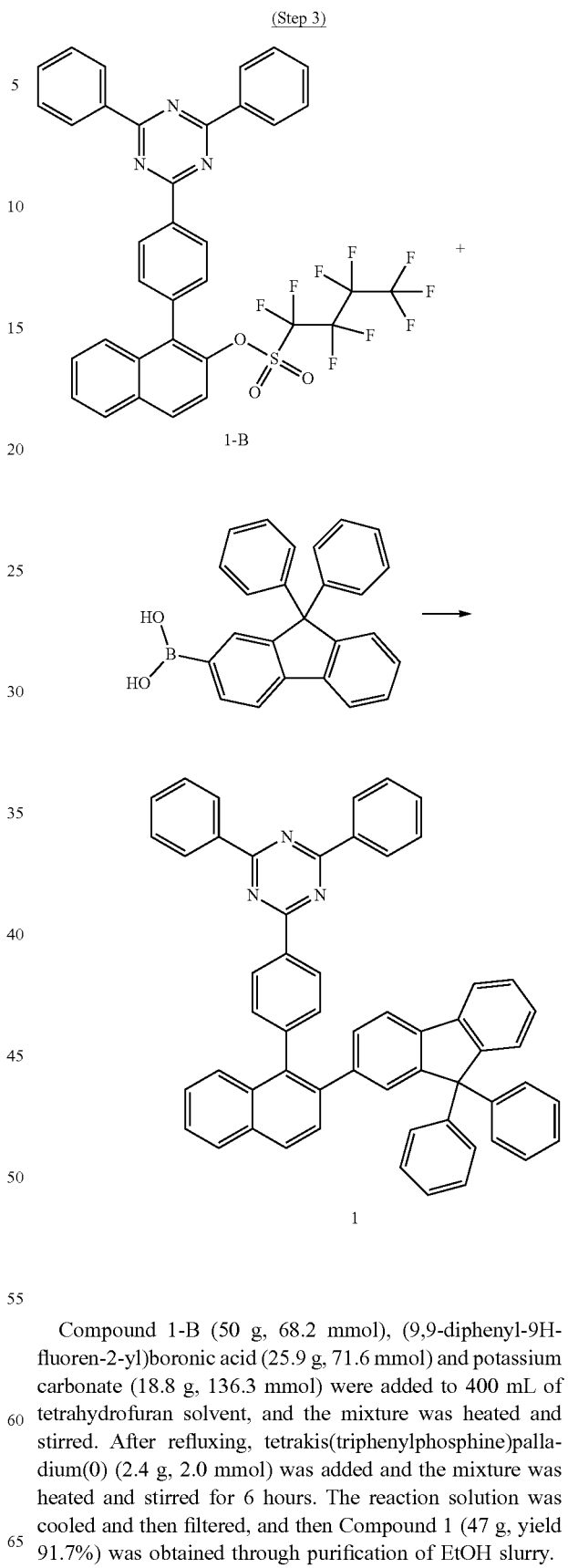

Compound 1-A (39 g, 86.4 mmol) and potassium carbonate (23.9 g, 172.7 mmol) were added to an acetonitrile solvent (300 mL) and heated to 50° C. After stirring for 30 minutes, 1,1,2,2,3,3,4,4,4-nonafluorobutane-1-sulfonyl fluoride (39.1 g, 129.6 mmol) was added, and the temperature was lowered to room temperature and the mixture was further stirred for 1 hour. After completion of the reaction, the impurities were mainly removed by filtration. Compound 1-B (60 g, yield 95%) was then prepared through an ethanol slurry

MS: [M+H]⁺=734

Compound 1-B (50 g, 68.2 mmol), (9,9-diphenyl-9H-fluoren-2-yl)boronic acid (25.9 g, 71.6 mmol) and potassium carbonate (18.8 g, 136.3 mmol) were added to 400 mL of tetrahydrofuran solvent, and the mixture was heated and stirred. After refluxing, tetrakis(triphenylphosphine)palladium(0) (2.4 g, 2.0 mmol) was added and the mixture was heated and stirred for 6 hours. The reaction solution was cooled and then filtered, and then Compound 1 (47 g, yield 91.7%) was obtained through purification of EtOH slurry.

MS: [M+H]⁺=752

Preparation Example 2: Preparation of Compound 3

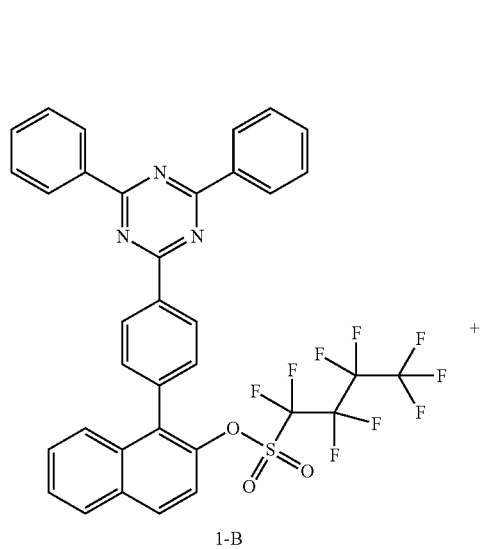

1-B

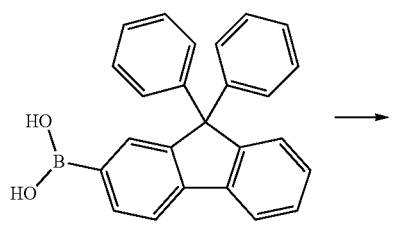

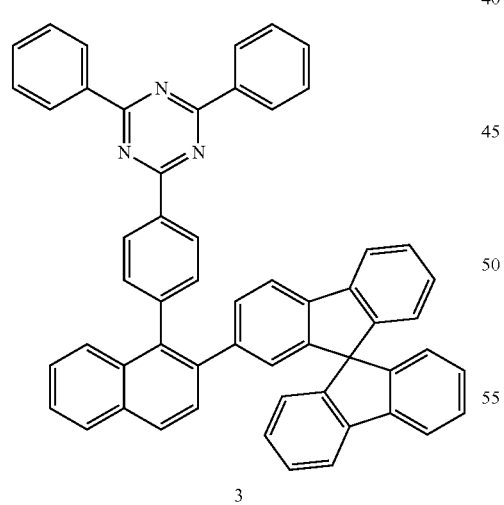

3

Compound 3 was prepared in the same manner as in the preparation method of Compound 1, except that 9,9'-spirobi[fluorene]-2-ylboronic acid was used instead of (9,9-diphenyl-9H-fluoren-2-yl)boronic acid.

MS: [M+H]$^+$=750

Preparation Example 3: Preparation of Compound 5

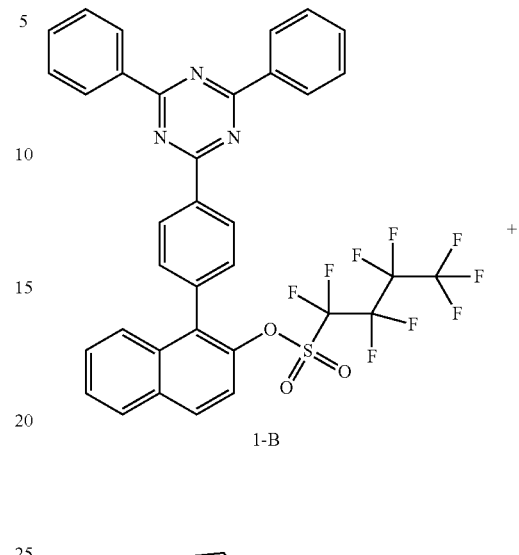

1-B

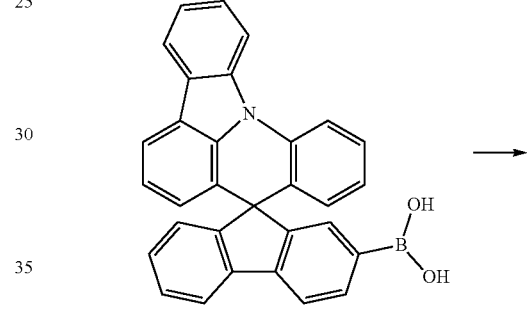

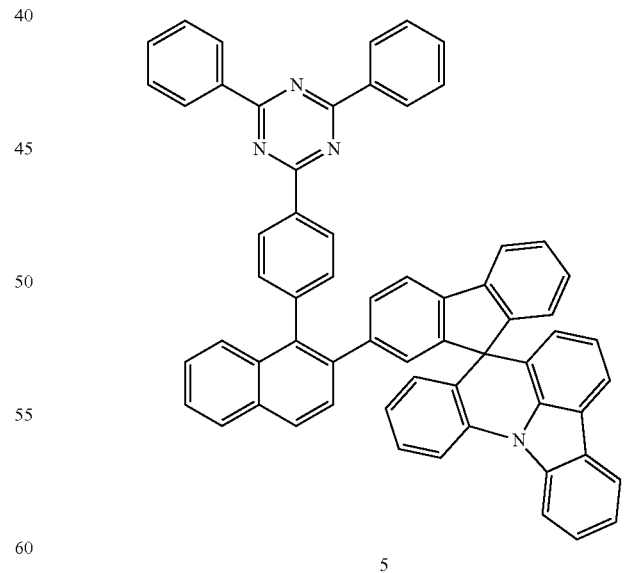

5

Compound 5 was prepared in the same manner as in the preparation method of Compound 1, except that spiro[fluorene-9,8'-indolo[3,2,1-de]acridine]-2-yl boronic acid was used instead of (9,9-diphenyl-9H-fluoren-2-yl)boronic acid.

MS: [M+H]$^+$=839

Preparation Example 4: Preparation of Compound 7

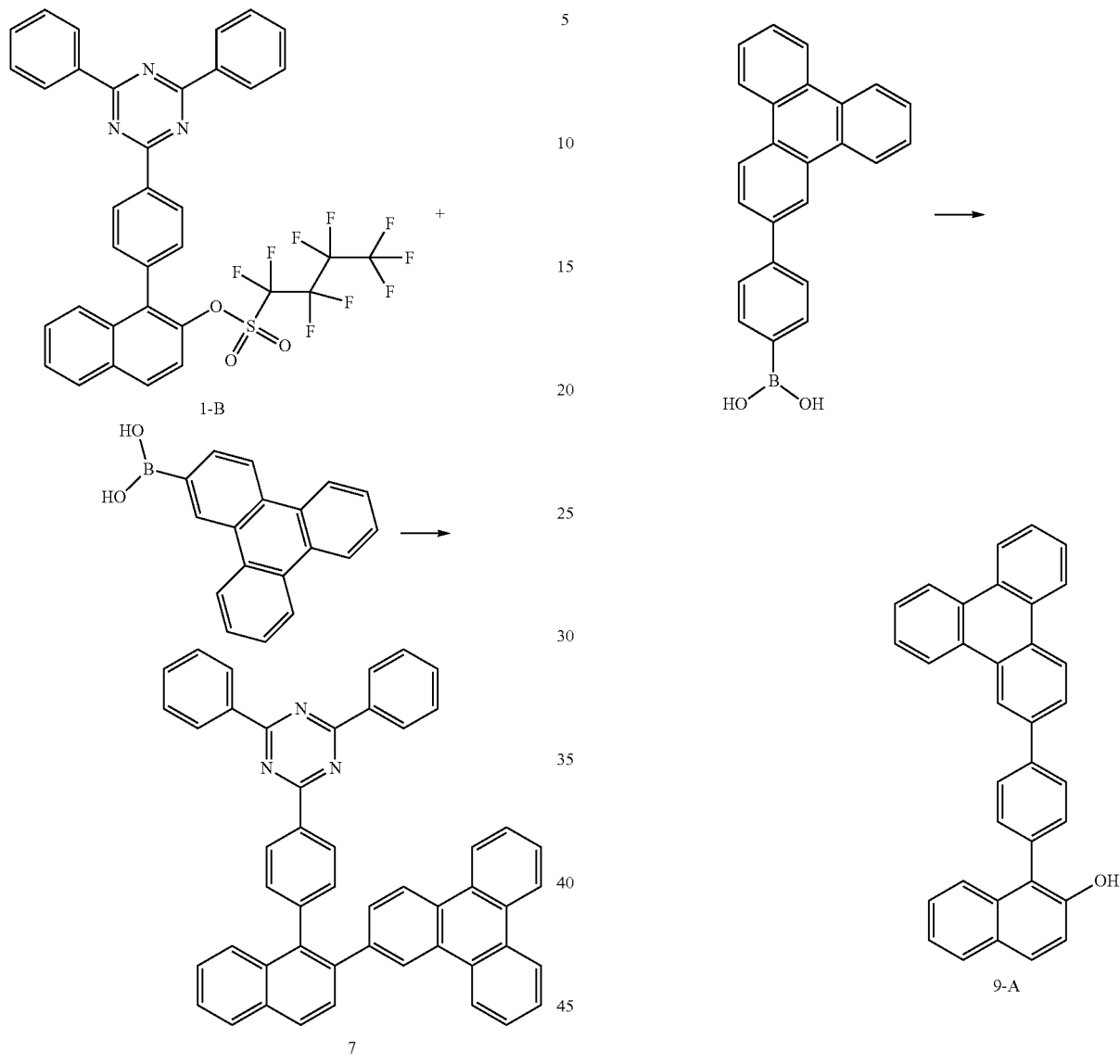

Compound 7 was prepared in the same manner as in the preparation method of Compound 1, except that triphenylene-2-ylboronic acid was used instead of (9,9-diphenyl-9H-fluoren-2-yl)boronic acid.

MS: [M+H]⁺=662

Preparation Example 5: Preparation of Compound 9

(Step 1)

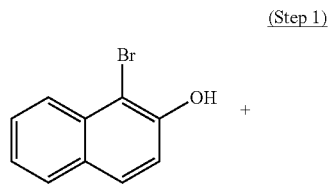

1-Bromonaphthalen-2-ol (20.0 g, 89.7 mmol), (4-(triphenylene-2-yl)phenyl)boronic acid (31.2 g, 89.7 mmol) and potassium carbonate (24.8 g, 179.3 mmol) were added and the mixture was heated and stirred. After refluxing, tetrakis (triphenylphosphine)palladium(0) (3.1 g, 2.6 mmol) was added thereto and the mixture was heated and stirred for further 3 hours. After completion of the reaction, the temperature was lowered to room temperature, and then the impurities were mainly removed by filtration. The filtrate was added in water and extracted with chloroform to obtain an organic layer, which was then dried over anhydrous magnesium sulfate. After distillation under reduced pressure, the residue was washed with ethanol to obtain Compound 9-A (38 g, yield 95%).

MS: [M+H]⁺=447

(Step 2)

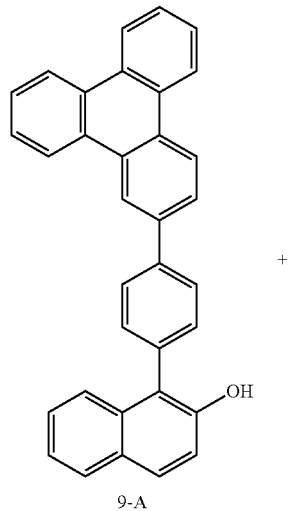

9-A

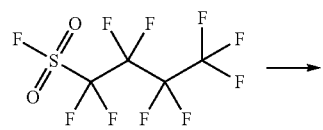

(Step 3)

9-B

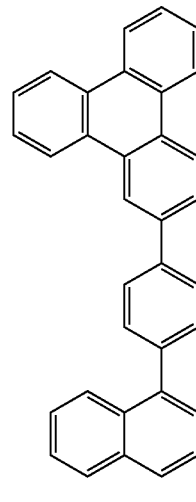

9-B

Compound 9-B was prepared in the same manner as in the preparation method of Compound 1-B, except that Compound 9-A was used instead of Compound 1-A.

MS: [M+H]⁺=729

9

Compound 9 was prepared in the same manner as in the preparation method of Compound 1, except that Compound 9-B was used instead of Compound 1-B and 2,4-diphenyl-6-(4-(4,4,5,5-tetramethyl-1,3,2-dioxaborolan-2-yl)phenyl)-1,3,5-triazine was used instead of (9,9-diphenyl-9H-fluoren-2-yl)boronic acid.

MS: [M+H]⁺=738

Preparation Example 6: Preparation of Compound 11

(Step 1)

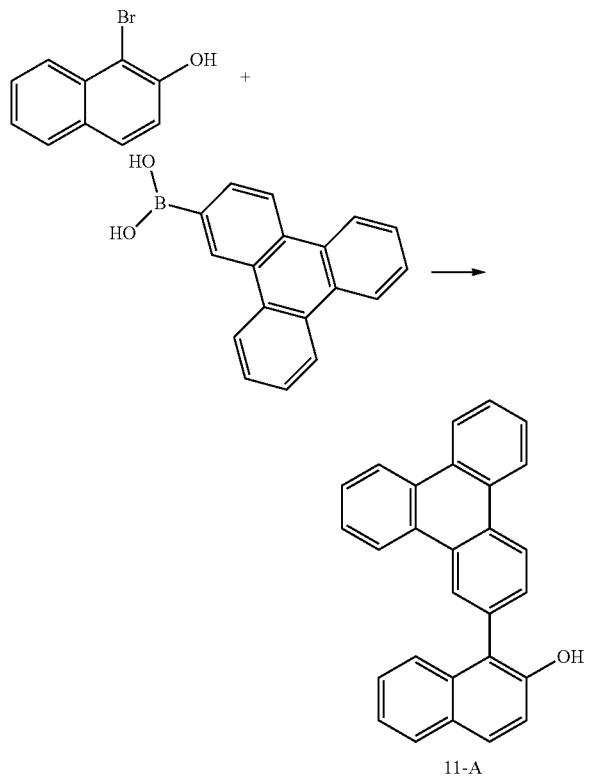

1-Bromonaphthalen-2-ol (20.0 g, 89.7 mmol), triphenylene-2-ylboronic acid (24.4 g, 89.7 mmol) and potassium carbonate (24.8 g, 179.3 mmol) were added and the mixture was heated and stirred. After refluxing, tetrakis(triphenylphosphine)palladium(0) (3.1 g, 2.6 mmol) was added thereto and the mixture was heated and stirred for further 3 hours. After completion of the reaction, the temperature was lowered, and then the impurities were mainly removed by filtration. The filtrate was added in water and extracted with chloroform to obtain an organic layer, which was then dried over anhydrous magnesium sulfate. After distillation under reduced pressure, the residue was washed with ethanol to obtain Compound 11-A (30 g, yield 91%).

MS: [M+H]$^+$=371

(Step 2)

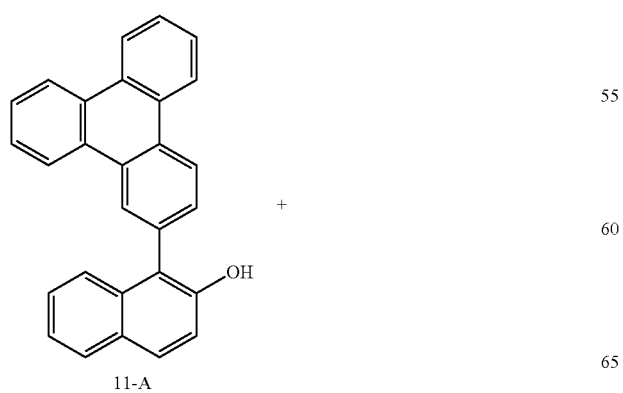

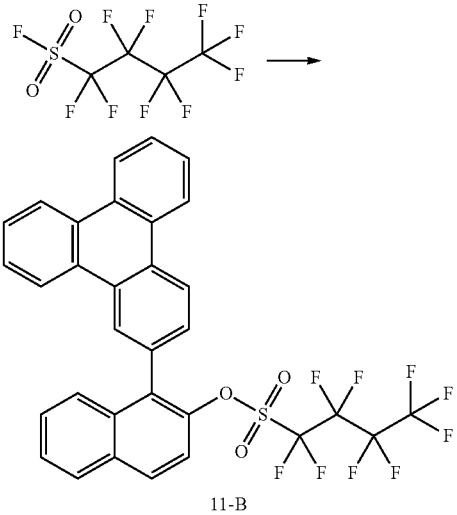

Compound 11-B was prepared in the same manner as in the preparation method of Compound 1-B, except that Compound 11-A was used instead of Compound 1-A.

MS: [M+H]$^+$=653

(Step 3)

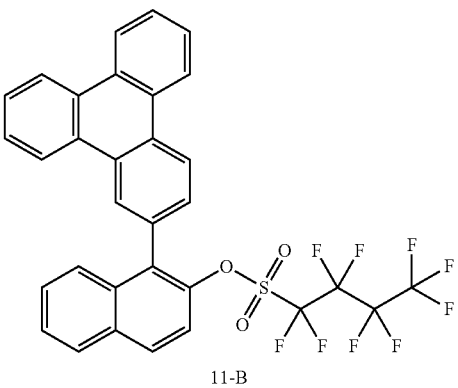

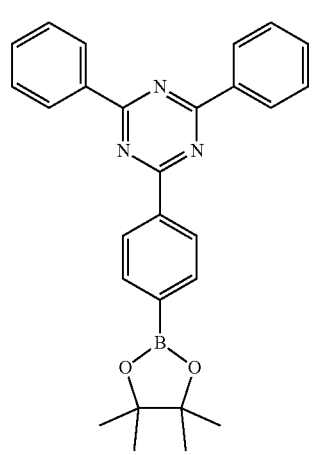

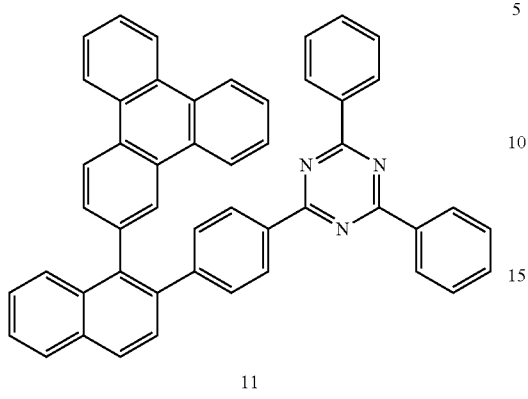

11

Compound 11-B (50 g, 76.6 mmol), 2,4-diphenyl-6-(4-(4,4,5,5-tetramethyl-1,3,2-dioxabororen-2-yl)phenyl)-1,3,5-triazine (33.4 g, 76.6 mmol), potassium carbonate (20.3 g, 153.2 mmol) and tetrakis(triphenylphosphine)palladium(0) (2.7 g, 2.3 mmol) were added, and the mixture was heated and stirred for 4 hours. After completion of the reaction, the reaction solution was cooled and then filtered, and then Compound 11 (47 g, yield 93%) was obtained through purification of EtOH slurry.

MS: [M+H]$^+$=662

Preparation Example 7: Preparation of Compound 13

(Step 1)

+

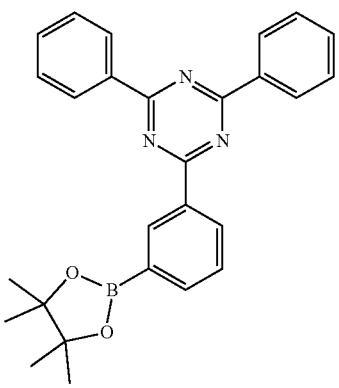

→

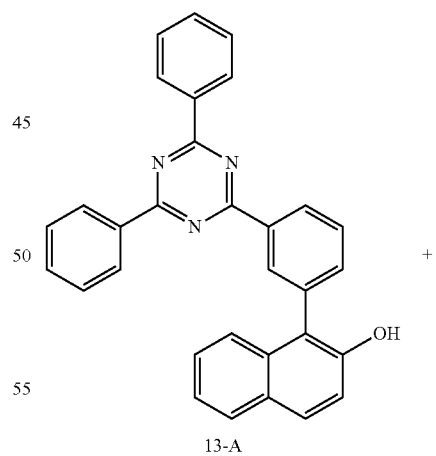

13-A

Compound 13-A was prepared in the same manner as in the preparation method of Compound 1-A, except that 2,4-diphenyl-6-(3-(4,4,5,5-tetramethyl-1,3,2-dioxaborolan-2-yl)phenyl)-1,3,5-triazine was used instead of 2,4-diphenyl-6-(4-(4,4,5,5-tetramethyl-1,3,2-dioxaborolan-2-yl)phenyl)-1,3,5-triazine.

MS: [M+H]$^+$=452

(Step 2)

13-A

+

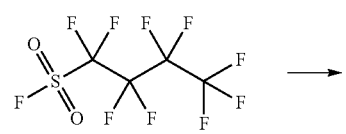

→

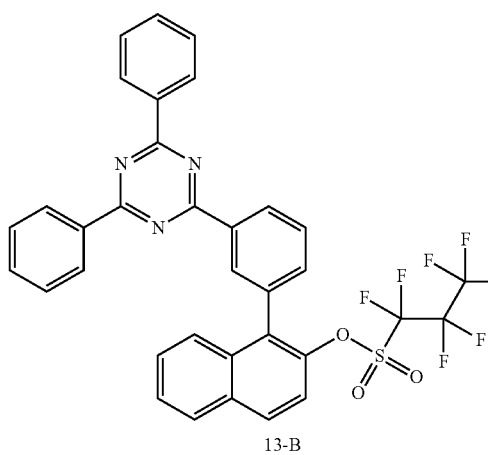

13-B

Compound 13-B was prepared in the same manner as in the preparation method of Compound 1-B, except that Compound 13-A was used instead of Compound 1-A.

MS: [M+H]⁺=734

(Step 3)

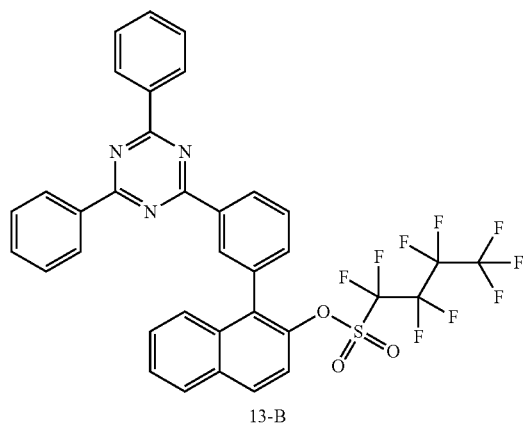

13-B

+

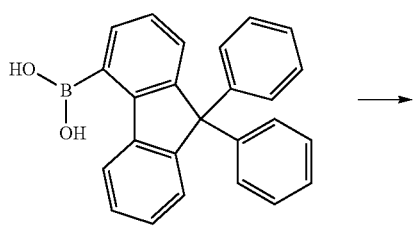

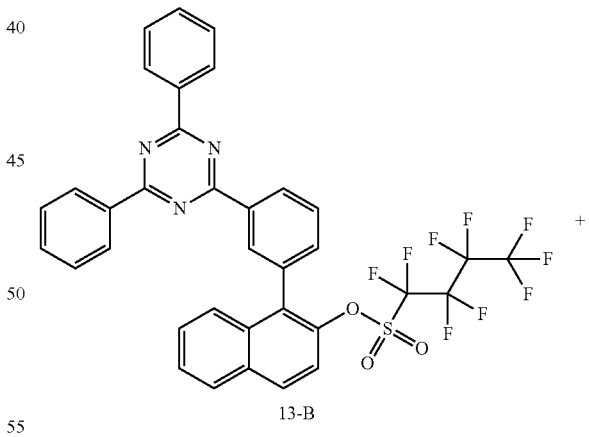

13

Compound 13 was prepared in the same manner as in the preparation method of Compound 1, except that Compound 13-B was used instead of Compound 1-B and (9,9-diphenyl-9H-fluoren-4-yl)boronic acid was used instead of (9,9-diphenyl-9H-fluoren-2-yl)boronic acid.

MS: [M+H]⁺=752

Preparation Example 8: Preparation of Compound 14

13-B

+

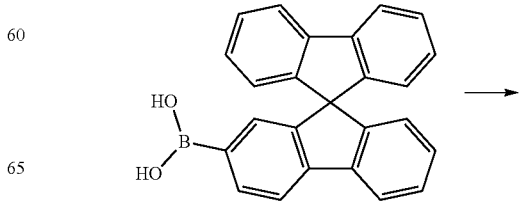

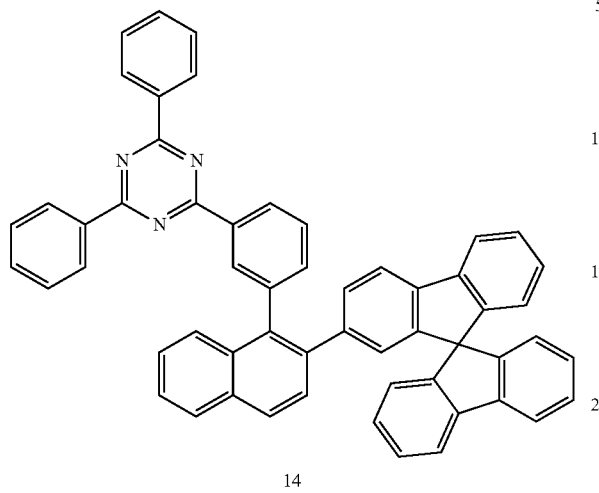

14

Compound 14 was prepared in the same manner as in the preparation method of Compound 13, except that 9,9'-spirobi[fluorene]-2-ylboronic acid was used instead of (9,9-diphenyl-9H-fluoren-4-yl)boronic acid.
MS: [M+H]⁺=750

Preparation Example 9: Preparation of Compound 18

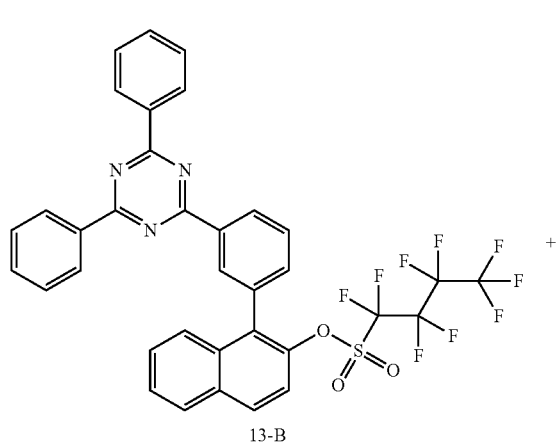

13-B

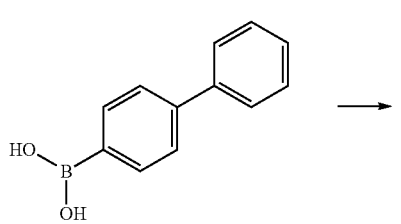

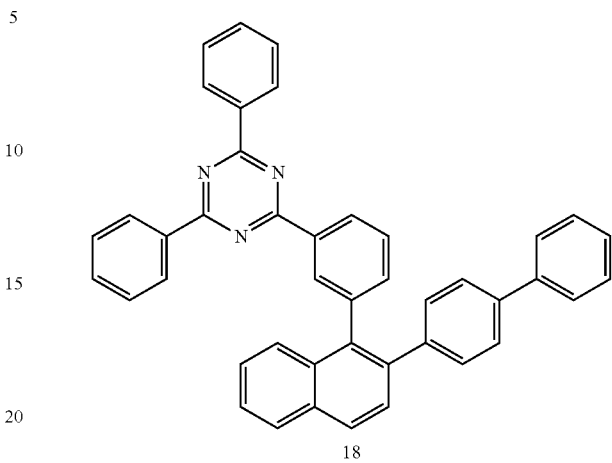

18

Compound 18 was prepared in the same manner as in the preparation method of Compound 13, except that [1,1'-biphenyl]-4-ylboronic acid was used instead of (9,9-diphenyl-9H-fluoren-4-yl)boronic acid.
MS: [M+H]⁺=588

Preparation Example 10: Preparation of Compound 19

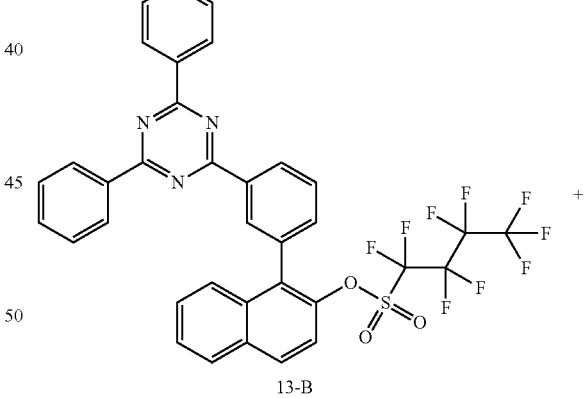

13-B

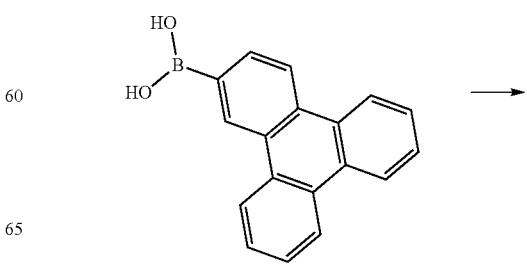

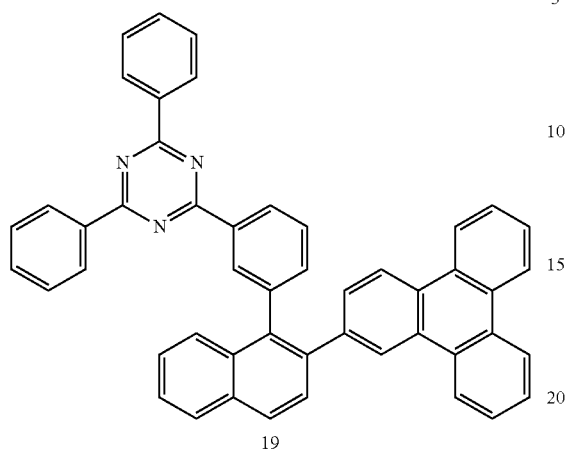

19

Compound 19 was prepared in the same manner as in the preparation method of Compound 7, except that Compound 13-B was used instead of Compound 1-B.

MS: [M+H]$^+$=662

Preparation Example 11: Preparation of Compound 50

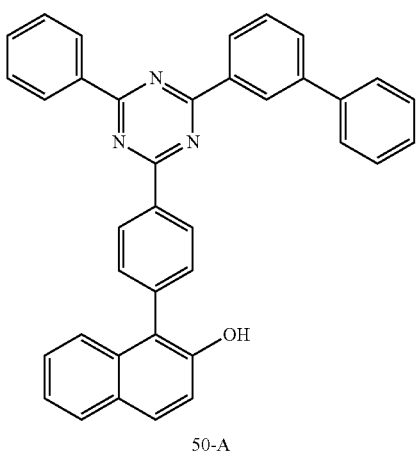

50-A

Compound 50-A was prepared in the same manner as in the preparation method of Compound 1-A, except that 2-([1,1'-biphenyl]-3-yl)-4-phenyl-6-(4-(4,4,5,5-tetramethyl-1,3,2-dioxaborolan-2-yl) phenyl)-1,3,5-triazine was used instead of 2,4-diphenyl-6-(4-(4,4,5,5-tetramethyl-1,3,2-dioxaborolan-2-yl)phenyl)-1,3,5-triazine.

MS: [M+H]$^+$=528

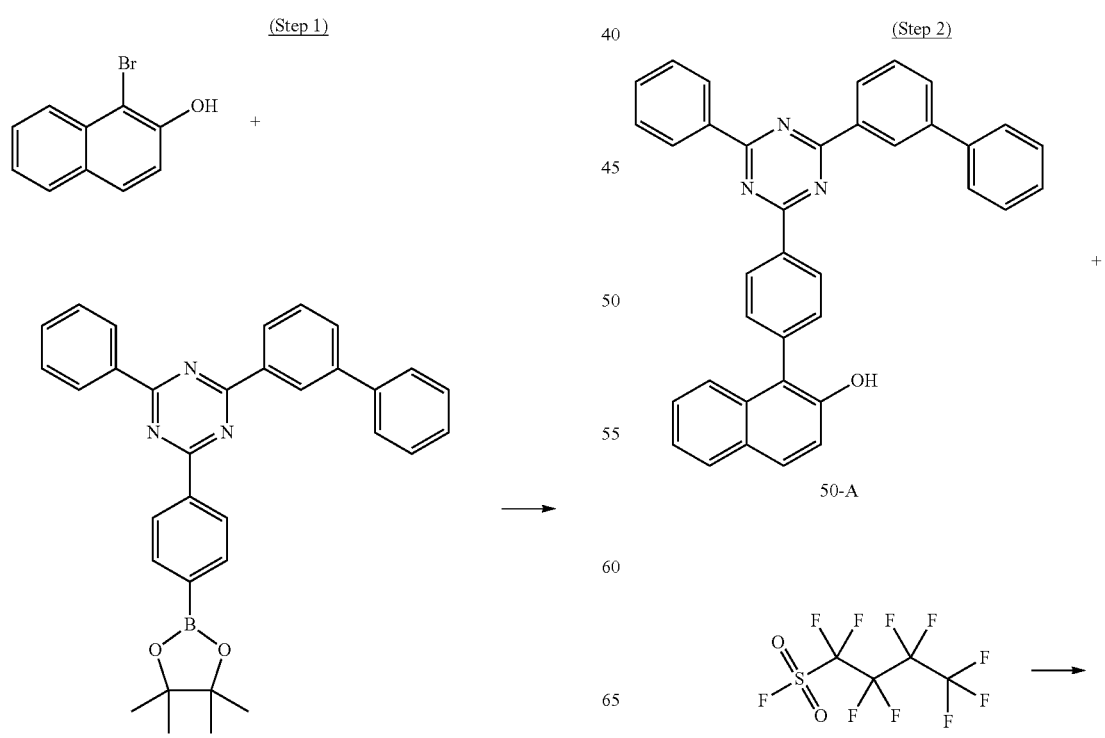

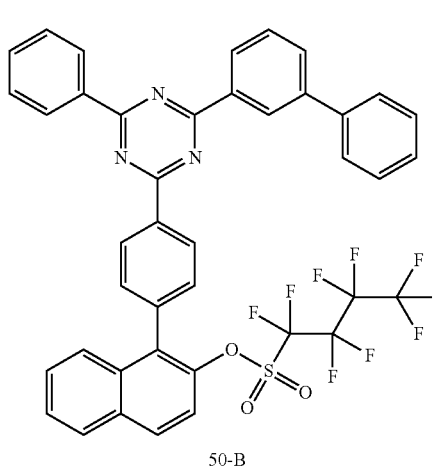

50-B

Compound 50-B was prepared in the same manner as in the preparation method of Compound 1-B, except that Compound 50-A was used instead of Compound 1-A.

MS: [M+H]$^+$=810

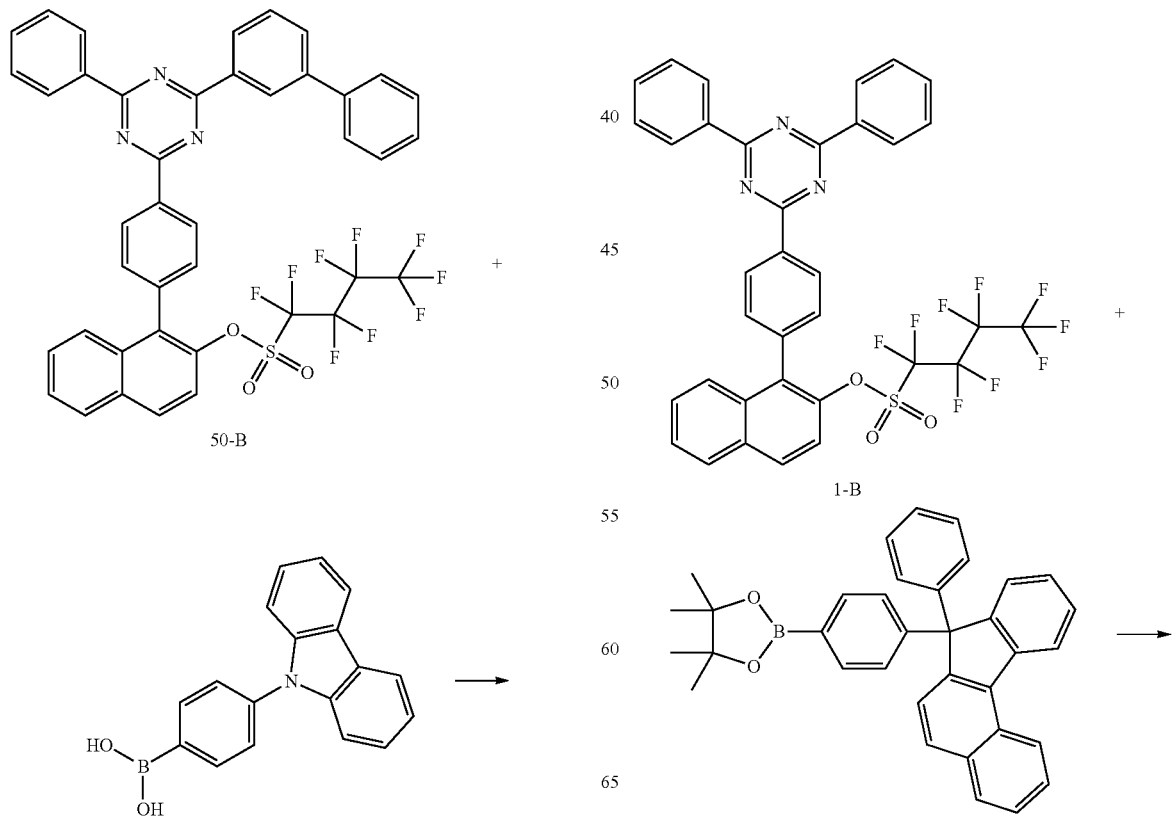

50

Compound 50 was prepared in the same manner as in the preparation method of Compound 1, except that (4-(9H-carbazole-9-yl)phenyl)boronic acid was used instead of (9,9-diphenyl-9H-fluoren-2-yl)boronic acid.

MS: [M+H]$^+$=753

Preparation Example 12: Preparation of Compound 66

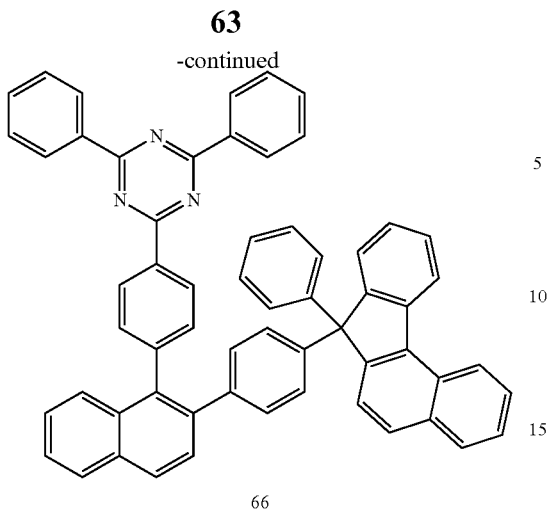

66

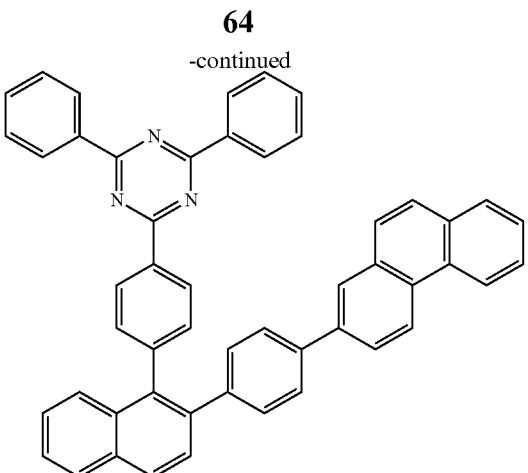

82

Compound 66 was prepared in the same manner as in the preparation method of Compound 1, except that 4,4,5,5-tetramethyl-2-(4-(7-phenyl-7H-benzo[c]fluoren-7-yl)phenyl)-1,3,2-dioxaborolane was used instead of (9,9-diphenyl-9H-fluoren-2-yl)boronic acid.

MS: [M+H]$^+$=802

Preparation Example 13: Preparation of Compound 82

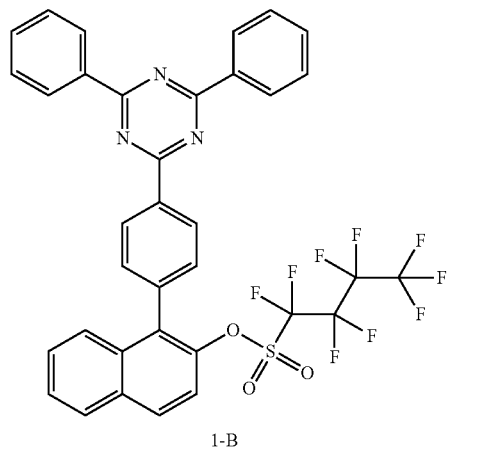

1-B

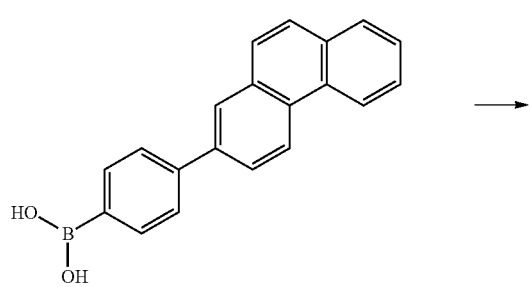

Compound 82 was prepared in the same manner as in the preparation method of Compound 1, except that (4-(phenanthrene-2-yl)phenyl)boronic acid was used instead of (9,9-diphenyl-9H-fluoren-2-yl)boronic acid.

MS: [M+H]$^+$=688

EXAMPLE

Example 1

The glass substrate (corning 7059 glass) on which a thin film of ITO (indium tin oxide) was applied in a thickness of 1,000 Å was put into distilled water having the detergent dissolved therein and washed by the ultrasonic wave. The used detergent was a product commercially available from Fisher Co. and the distilled water was one which had been twice filtered by using a filter commercially available from Millipore Co. The ITO was washed for 30 minutes, and washing with ultrasonic waves was then repeated twice for 10 minutes by using distilled water. After the washing with distilled water was finished, washing with ultrasonic waves was performed in the order of isopropyl alcohol, acetone, and methanol solvent, and dried. Hexanitrile hexaazatriphenylene was thermally deposited under vacuum in a thicknesses of 500 Å on the ITO transparent electrode thus prepared to form the hole injection layer. HT1 (400 Å), which is a hole transport material, was deposited under vacuum thereon, and a host H1 and a dopant D1 compound were deposited under vacuum as a light emitting layer in a thickness of 300 Å. Compound 1 prepared in Preparation Example 1 and LiQ (Lithium Quinolate) were deposited under vacuum at a weight ratio of 1:1 on the light emitting layer to form an electron injection and transport layer having a thickness of 350 Å. Lithium fluoride (LiF) with a thickness of 12 Å and aluminum with a thickness of 2,000 Å were sequentially deposited on the electron injection and transport layer to form a cathode, thereby preparing an organic light emitting device.

In the above process, the vapor deposition rate of the organic material was maintained at 0.4 to 0.7 Å/sec, the deposition rate of the lithium fluoride of the cathode was maintained at 0.3 Å/sec, the deposition rate of the aluminum was maintained at 2 Å/sec, and the degree of vacuum during vapor deposition was maintained at $2 \times 10^{-7}$ to $5 \times 10^{-6}$ torr, thereby fabricating an organic light emitting device. Further, the structures of the compounds used were as follows.

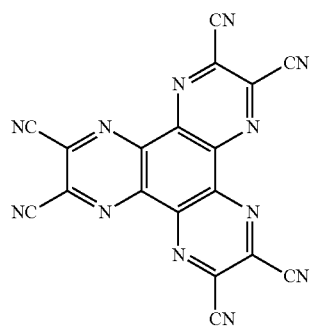
Hexanitrile hexaazatriphenylene

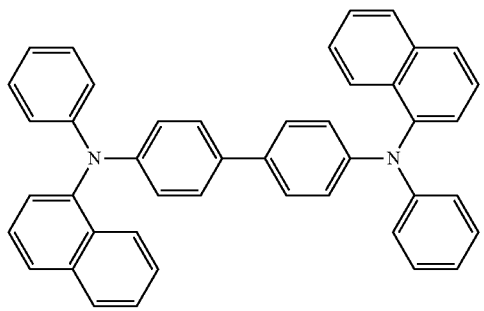
HT1

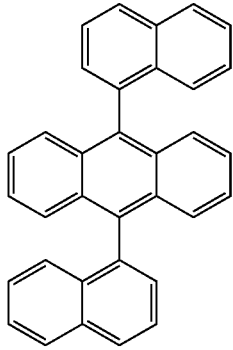
H1

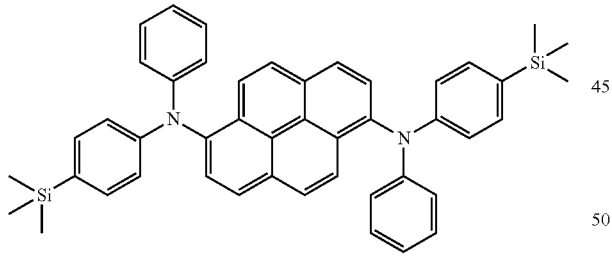
D1

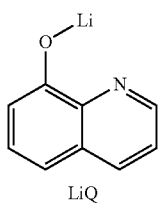
LiQ

Examples 2 to 13

An organic light emitting device was prepared in the same manner as in Example 1, except that the compound described in Table 1 below was used instead of Compound 1 as the electron transport layer.

Comparative Examples 1 to 5

An organic light emitting device was prepared in the same manner as in Example 1, except that the following compounds ET1, ET2, ET3, ET4, and ET5 were respectively used instead of Compound 1 as the electron transport layer.

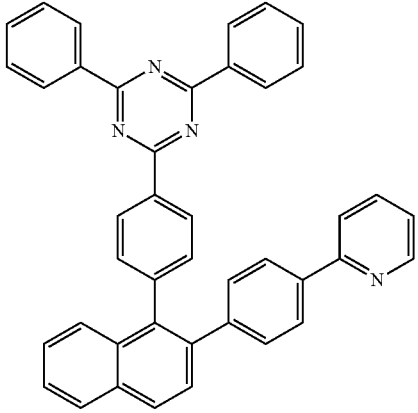
ET1

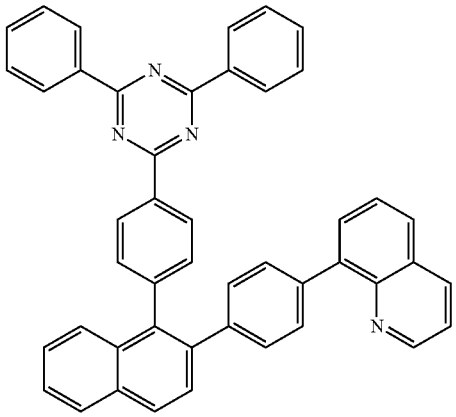
ET2

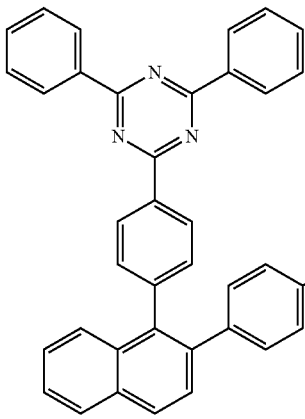
ET3

ET4

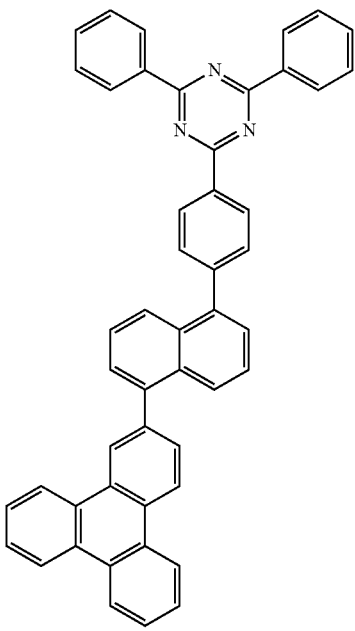

ET5

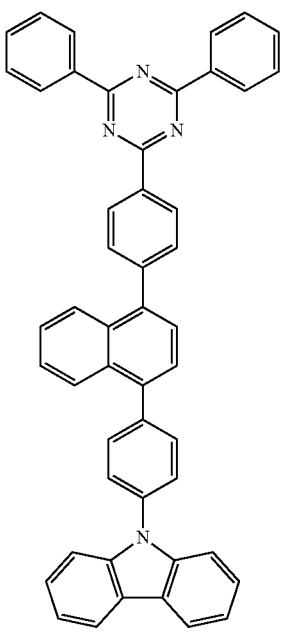

Experimental Example

For the organic light emitting devices of Examples 1 to 13 and Comparative Examples 1 to 5, the driving voltage and the light emitting efficiency were measured at a current density of 10 mA/cm$^2$, and a time (LT98) for reaching a 98% value compared to the initial luminance was measured at a current density of 20 mA/cm$^2$. The results are shown in Table 1 below.

TABLE 1

| | Compound | Voltage (V) | Current efficiency (cd/A) | Color coordinate (x, y) | Life Time (98 at 20 mA/cm$^2$) |
|---|---|---|---|---|---|
| Example 1 | 1 | 3.67 | 5.64 | (0.134, 0.106) | 83 |
| Example 2 | 3 | 3.68 | 5.86 | (0.134, 0.106) | 88 |
| Example 3 | 5 | 3.83 | 4.89 | (0.134, 0.107) | 108 |
| Example 4 | 7 | 3.98 | 4.87 | (0.134, 0.106) | 186 |
| Example 5 | 9 | 4.02 | 4.72 | (0.134, 0.107) | 229 |
| Example 6 | 11 | 3.98 | 4.73 | (0.134, 0.106) | 317 |
| Example 7 | 13 | 3.68 | 5.66 | (0.134, 0.106) | 80 |
| Example 8 | 14 | 3.72 | 5.57 | (0.134, 0.106) | 82 |
| Example 9 | 18 | 3.82 | 4.69 | (0.134, 0.106) | 77 |
| Example 10 | 19 | 3.91 | 4.80 | (0.134, 0.106) | 220 |
| Example 11 | 50 | 4.11 | 4.66 | (0.134, 0.107) | 85 |
| Example 12 | 66 | 3.78 | 5.51 | (0.134, 0.107) | 89 |
| Example 13 | 82 | 3.99 | 4.70 | (0.134, 0.106) | 80 |
| Comparative Example 1 | ET1 | 4.73 | 3.89 | (0.134, 0.107) | 47 |
| Comparative Example 2 | ET2 | 4.91 | 3.96 | (0.135, 0.107) | 38 |
| Comparative Example 3 | ET3 | 4.88 | 3.68 | (0.135, 0.106) | 44 |
| Comparative Example 4 | ET4 | 4.89 | 3.79 | (0.134, 0.106) | 36 |
| Comparative Example 5 | ET5 | 4.67 | 3.92 | (0.135, 0.107) | 45 |

From the results shown in Table 1, it was confirmed that the compound represented by Chemical Formula 1 according to one embodiment of the present invention can be used for an organic material layer capable of simultaneously performing electron injection and electron transport of the organic light emitting device.

In addition, it was confirmed through Examples and Comparative Examples that, when triazine and linker-aryl, or linker heteroaryl substituent groups are positioned at the positions 1/2 or positions 2/1 of naphthalene as in one embodiment of the present specification, an organic light emitting device having a low driving voltage, high efficiency and long life time can be provided.

Specifically, as shown in Comparative Examples 1 to 3, although the substituent group was substituted at positions 1 and 2 of naphthalene, the case where substituted functional group is aryl group exhibited excellent characteristics in terms of driving voltage, efficiency and life time as compared with the case where the substituted functional group is hetero aryl (pyridine, quinoline, phenanthroline). In addition, as shown in Comparative Examples 4 to 5, although triazine and the like functional groups were present, it was confirmed that when naphthalene was substituted at positions 1 and 2, the characteristics of the light emitting device were excellent as compared with when it was substituted at different positions.

The compound represented by Chemical Formula 1 according to one embodiment of the present invention has excellent thermal stability, a deep HOMO level of 6.0 eV or more, a high triplet energy (ET) and a hole stability, and thereby exhibited remarkably excellent characteristics in terms of the driving voltage, luminous efficiency and life time.

EXPLANATION OF SIGN

1: substrate   2: anode
3: light emitting layer   4: cathode

-continued

| 5: hole injection layer | 6: hole transport layer |
| 7: light emitting layer | 8: electron transport layer |

The invention claimed is:
1. A compound represented by Chemical Formula 1 below:

[Chemical Formula 1]

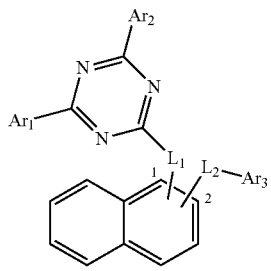

In Chemical Formula 1,
$L_1$ and $L_2$ are bonded at positions 1 and 2 of naphthalene, or bonded at positions 2 and 1 of naphthalene,
$L_1$ is a substituted or unsubstituted $C_{6-60}$ arylene; or a substituted or unsubstituted $C_{2-60}$ heteroarylene containing at least one of O, N, Si and S,
$L_2$ is a bond; a substituted or unsubstituted $C_{6-60}$ arylene; or a substituted or unsubstituted $C_{2-60}$ heteroarylene containing at least one of O, N, Si and S,
$Ar_1$ and $Ar_2$ are each independently a substituted or unsubstituted $C_{6-60}$ aryl; or a substituted or unsubstituted $C_{2-60}$ heteroaryl containing at least one of O, N, Si and S, and
$Ar_3$ is a unsubstituted $C_{2-60}$ heteroaryl containing at least one of O, N, Si and S, or one selected from the group consisting of:

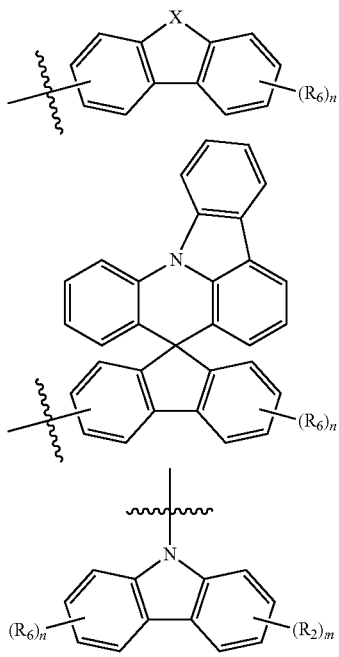

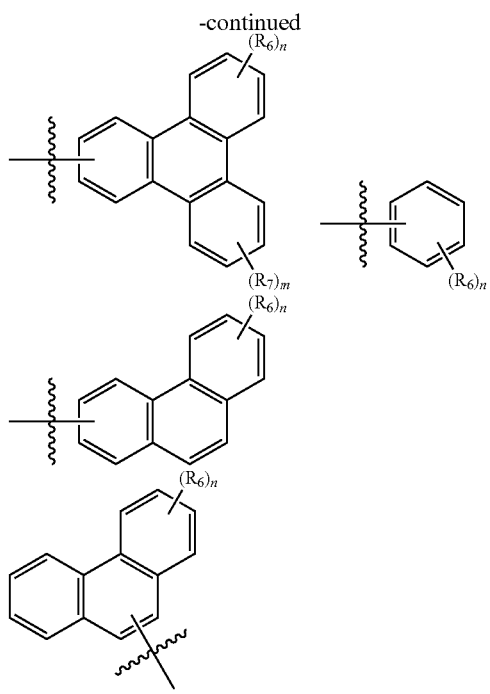

wherein,
X is $NR_1$, $SiR_4R_5$, S, or O,
$R_1$, $R_2$, $R_4$ to $R_7$ are each independently hydrogen, deuterium, halogen, nitrile, nitro, amino; substituted or unsubstituted $C_{1-60}$ alkyl, substituted or unsubstituted $C_{3-60}$ cycloalkyl, substituted or unsubstituted $C_{2-60}$ alkenyl, substituted or unsubstituted $C_{6-60}$ aryl, or substituted or unsubstituted $C_{2-60}$ heterocyclic group containing one or more of O, N, Si and S,
n and m are each independently an integer of 0 to 4,
with the proviso that $Ar_3$ does not have pyridine, quinoline, isoquinoline, phenanthridine, benzo[f]quinoline, benzo[f]isoquinoline, benzo[h]quinoline or benzo[h]isoquinoline structures.
2. The compound of claim 1,
wherein $L^1$ is phenylene.
3. The compound of claim 1,
wherein $L_2$ is a bond, or phenylene.
4. The compound of claim 1,
wherein $Ar_1$ is phenyl.
5. The compound of claim 1,
wherein $Ar_2$ is phenyl, or biphenyl.
6. The compound of claim 1,
wherein $Ar_3$ is any one selected from the group consisting of:

(c)

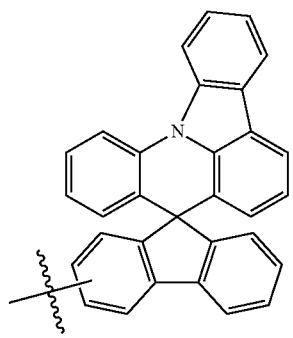

-continued
(d)
(e)
(f)
(g)
(h)
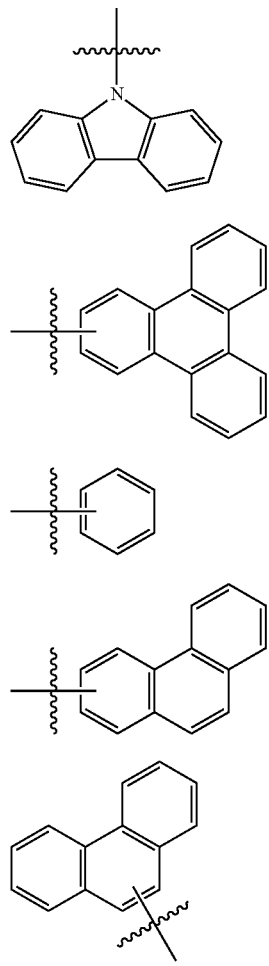
7. The compound of claim 1,
wherein the compound is selected from the group consisting of the following compounds:
5
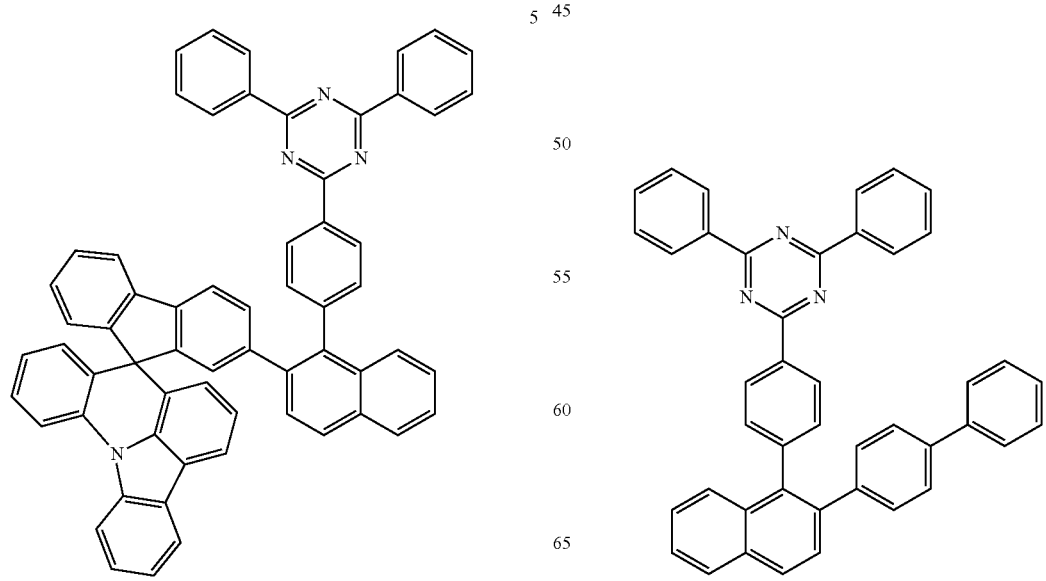
-continued
6
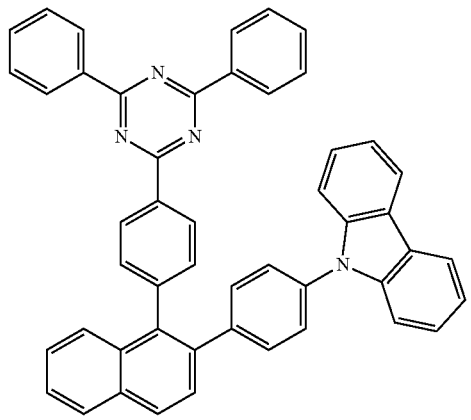
7
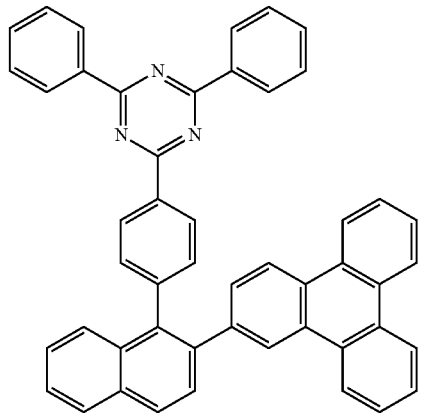
8

9
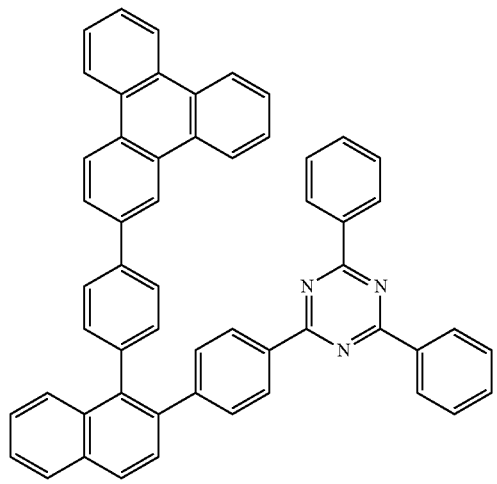
10
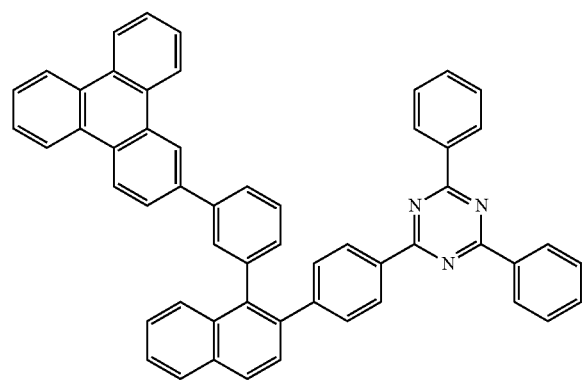
11
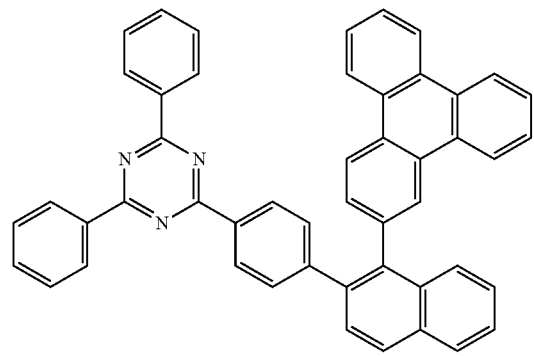
16
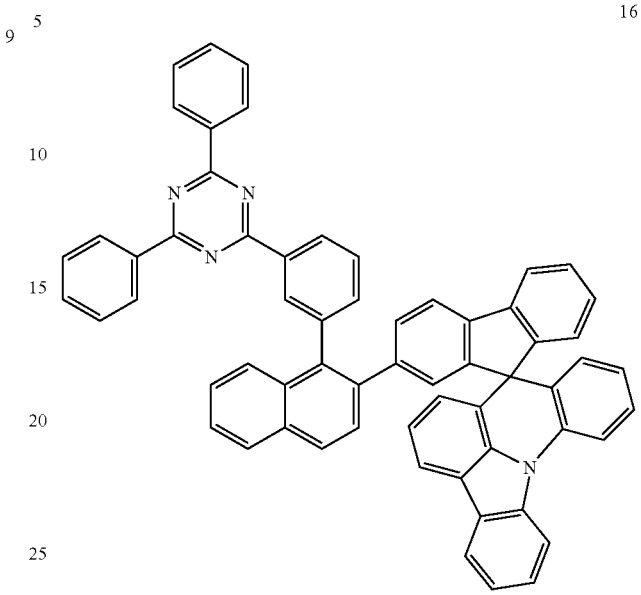
17
18
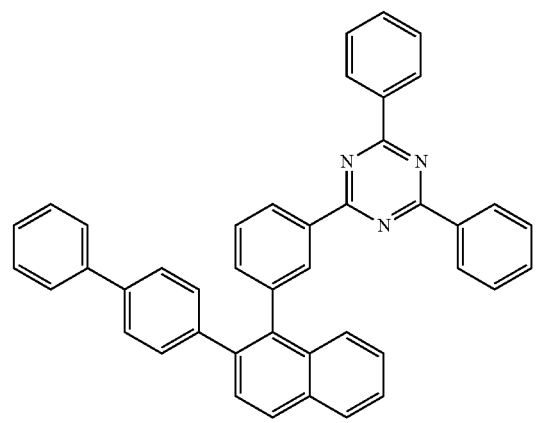

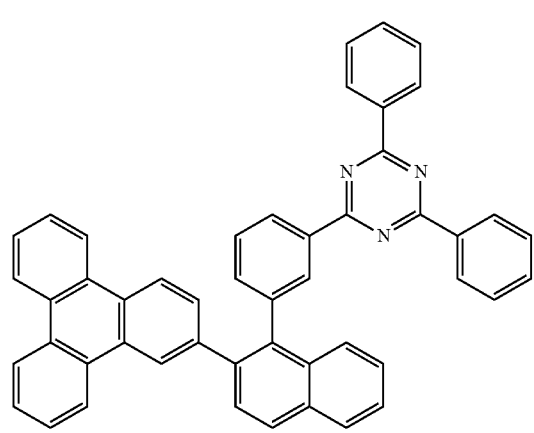
19
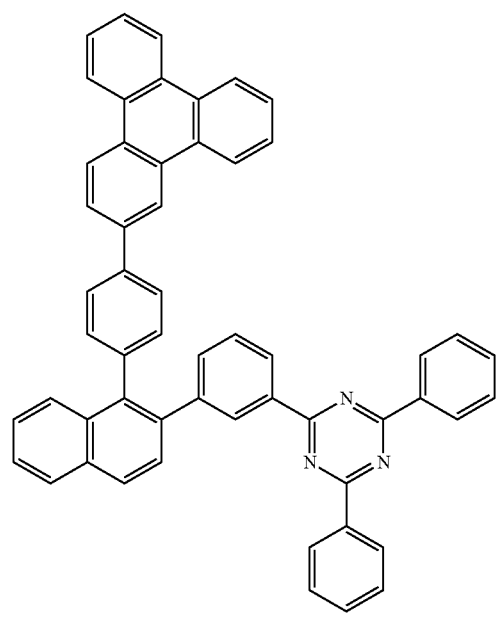
20
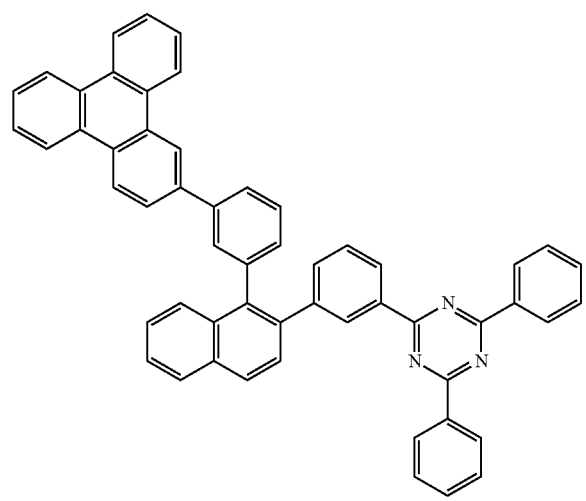
21
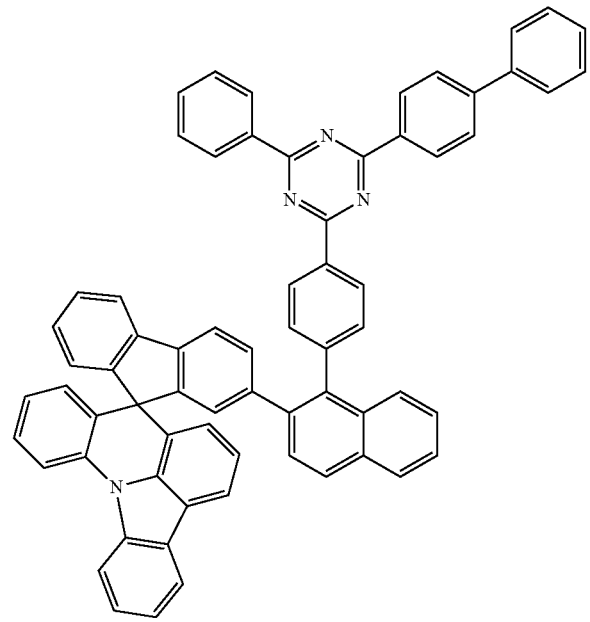
26
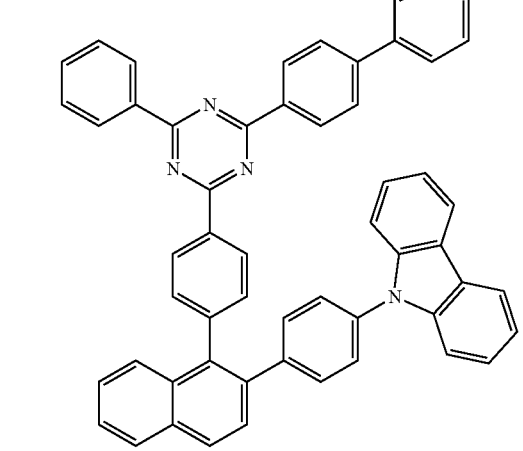
27
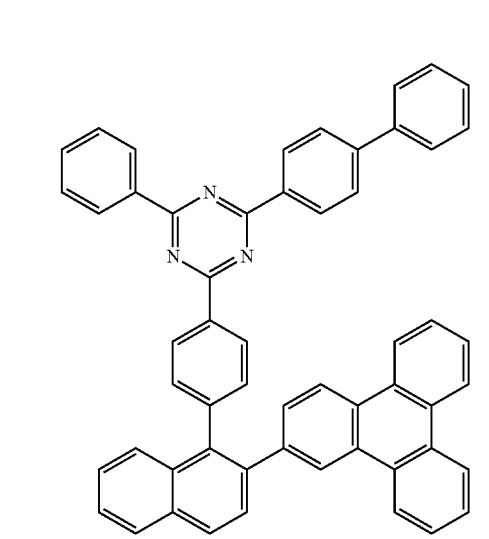
28

29
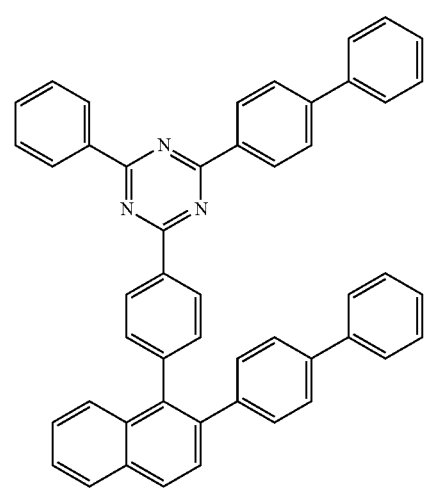
30
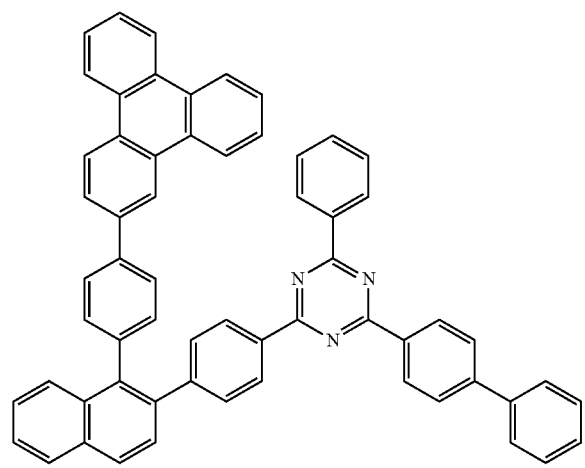
31
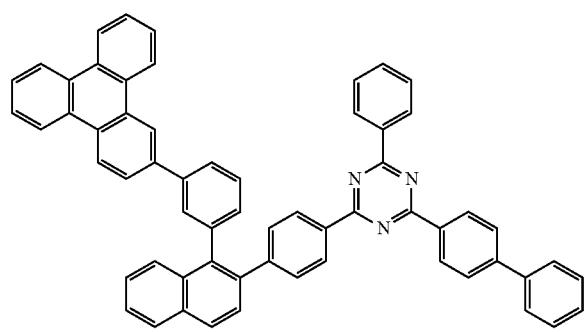
32
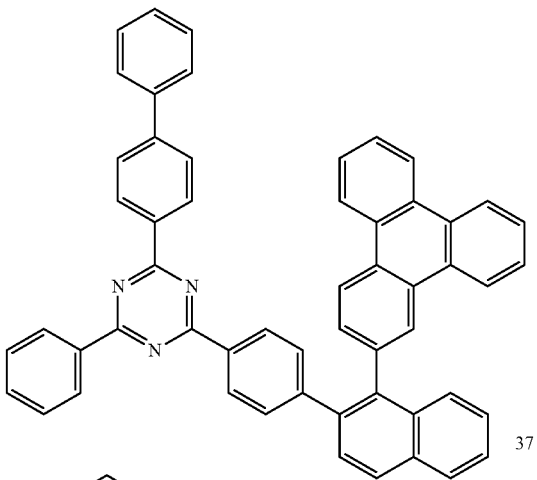
37
38
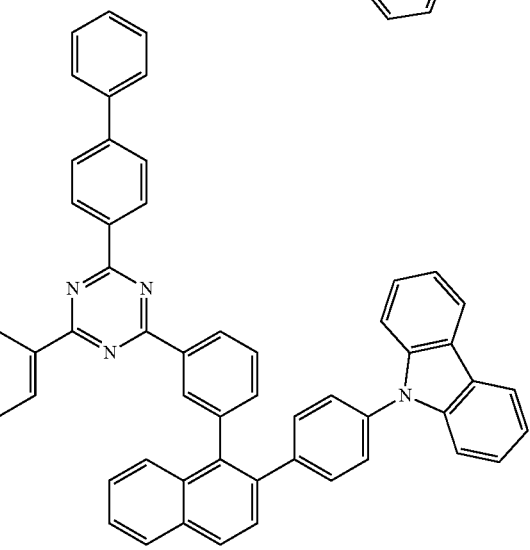

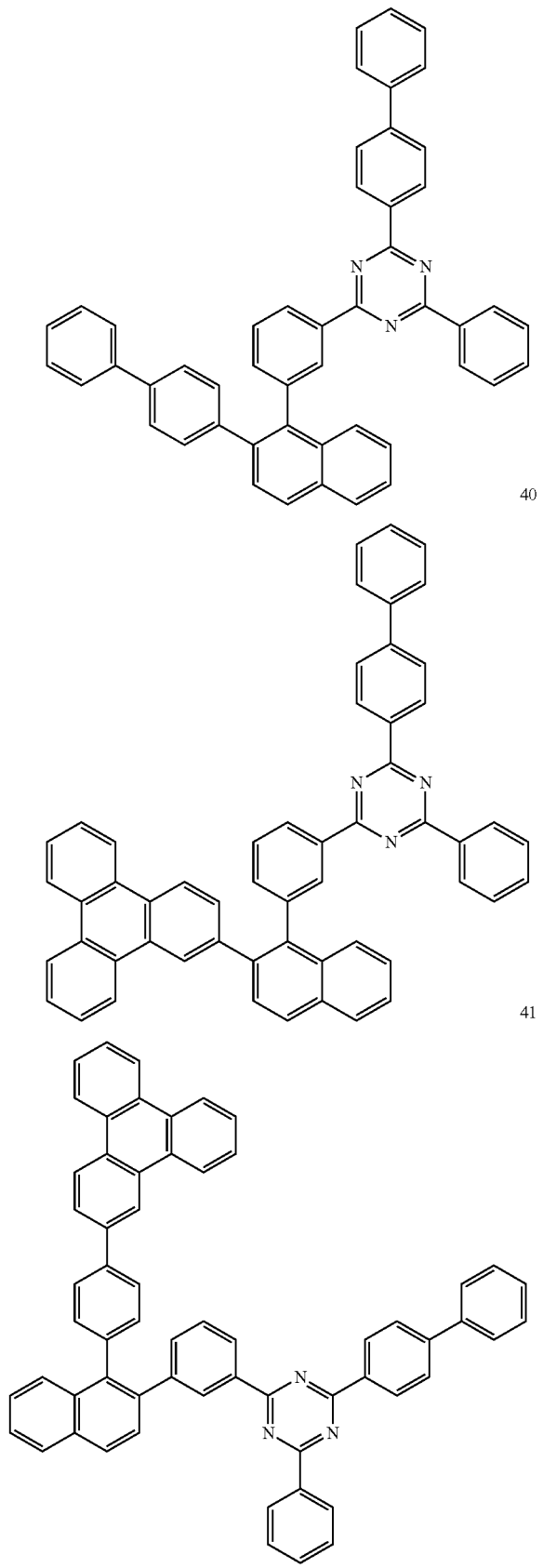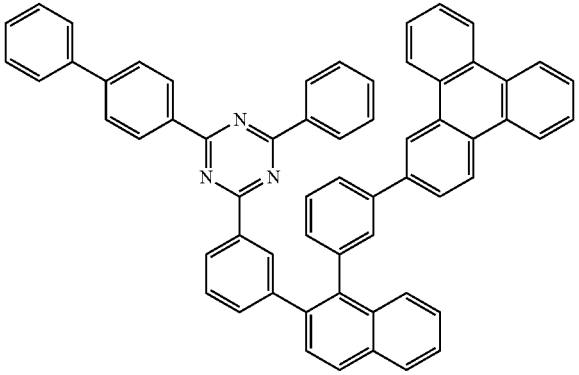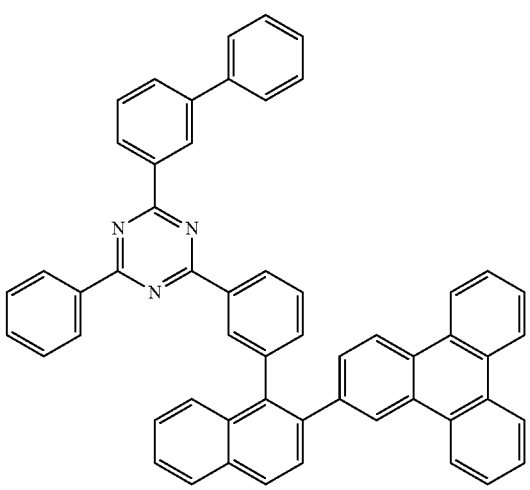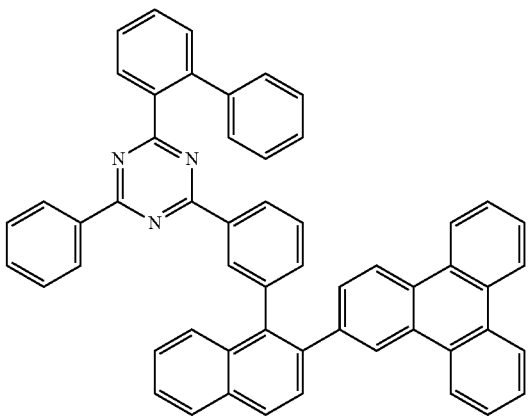

81
-continued
49
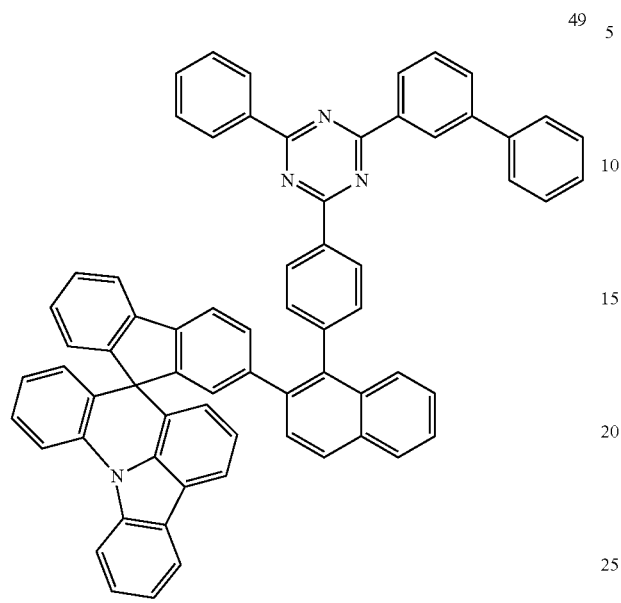
50
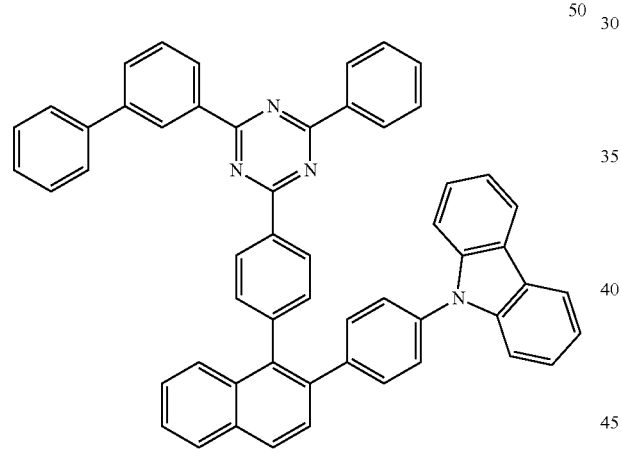
51
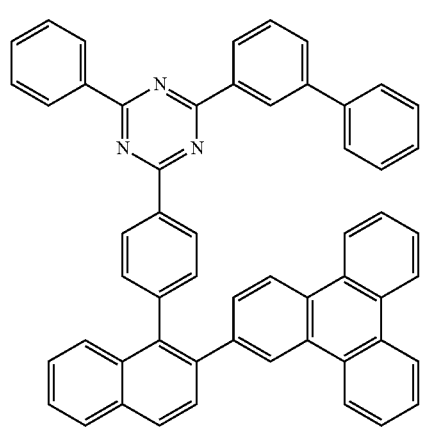
82
-continued
52
53
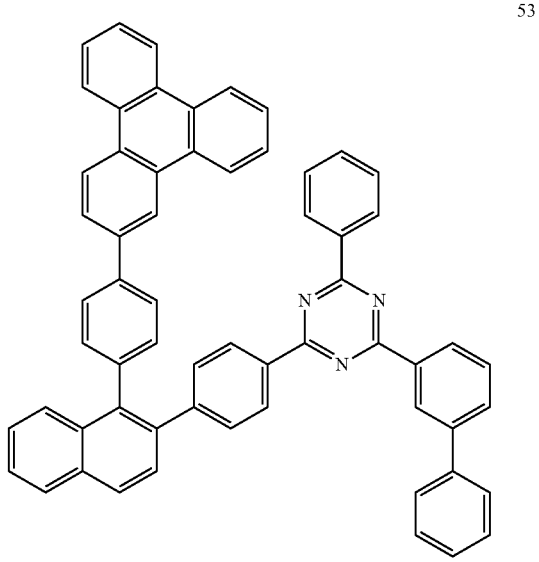
54
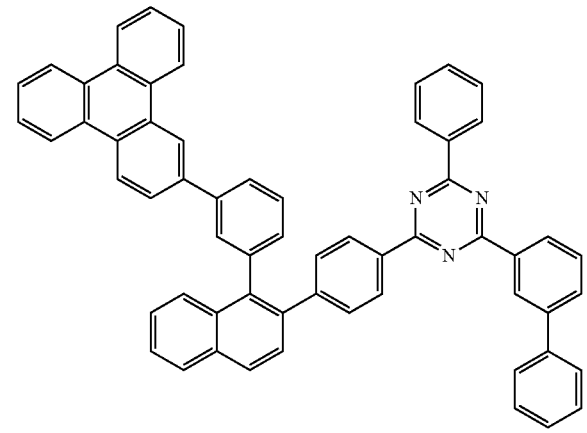

55
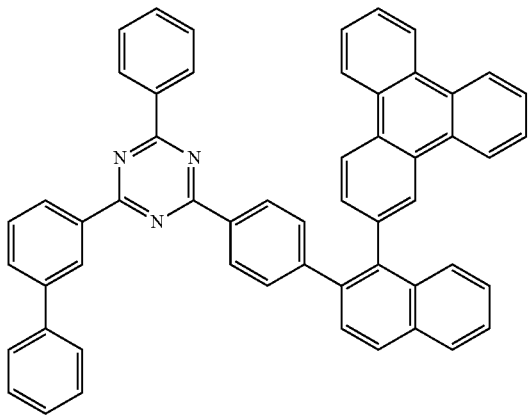
60
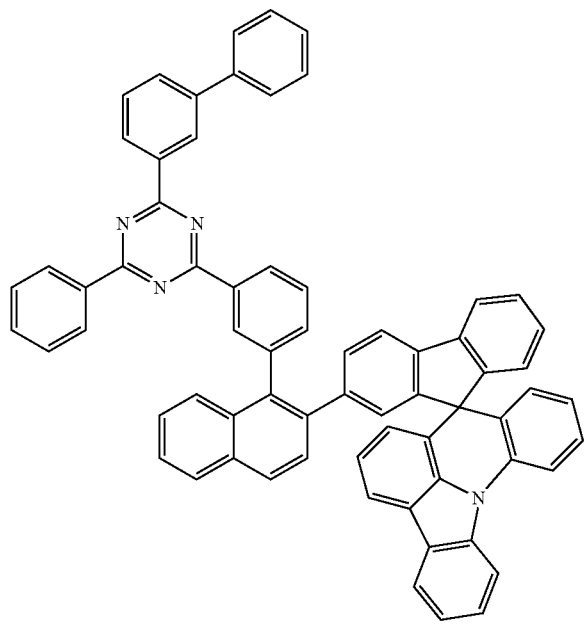
61
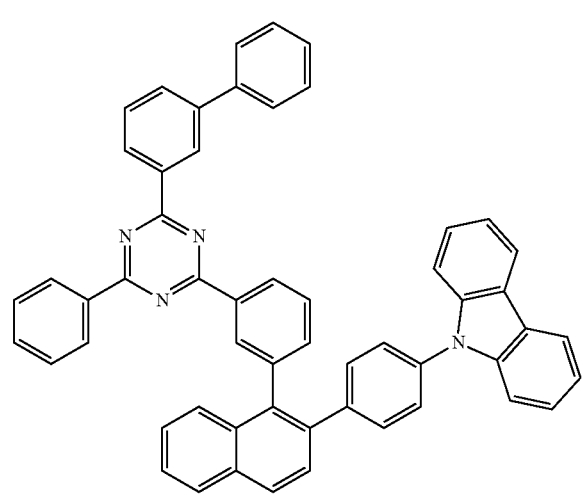
62
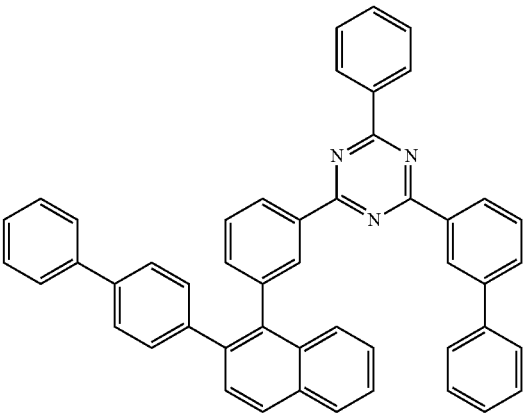
63
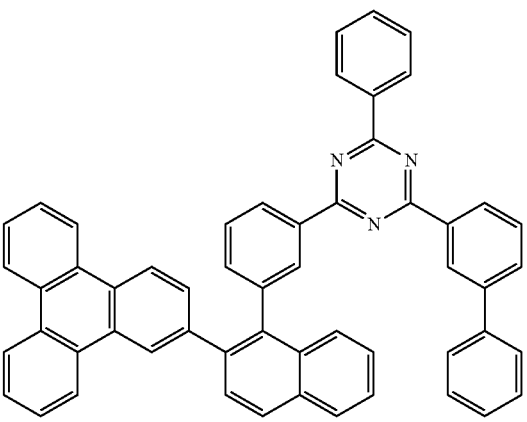
64
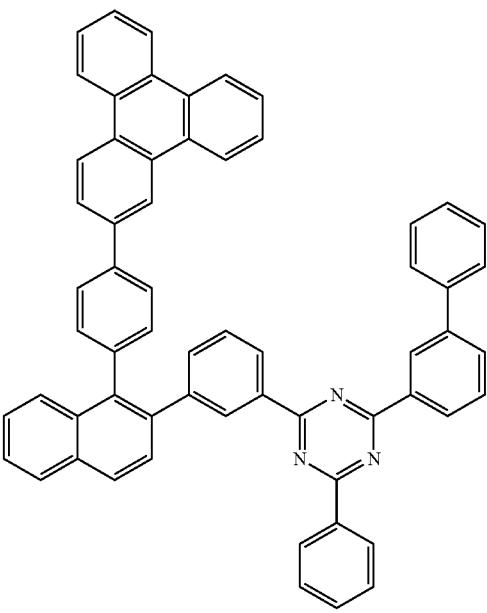

65
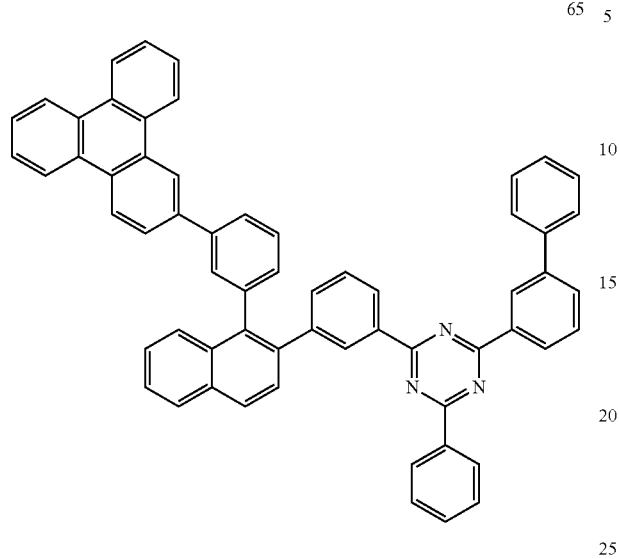
70
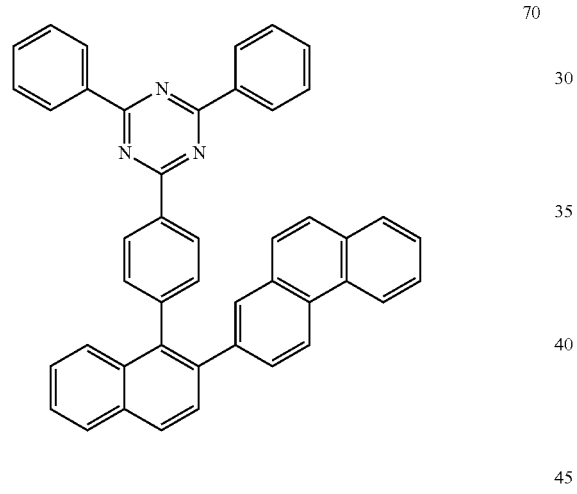
71
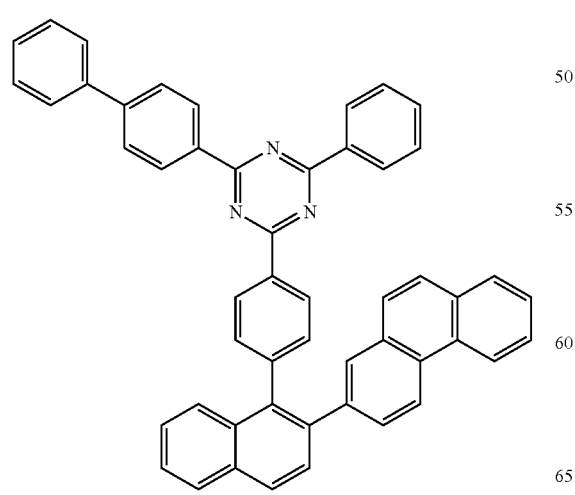
72
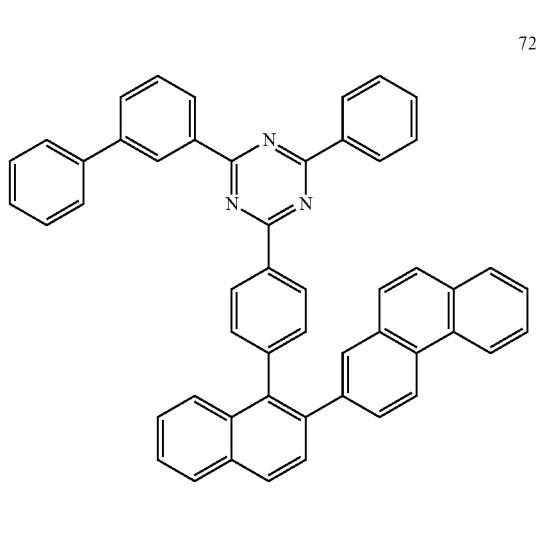
73
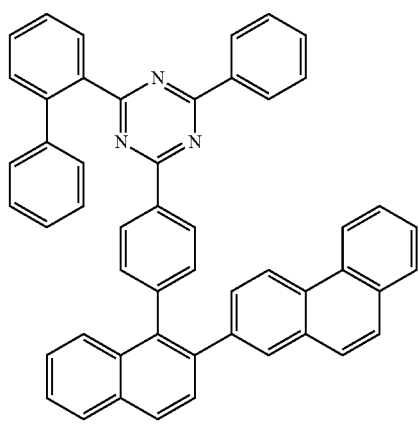
74
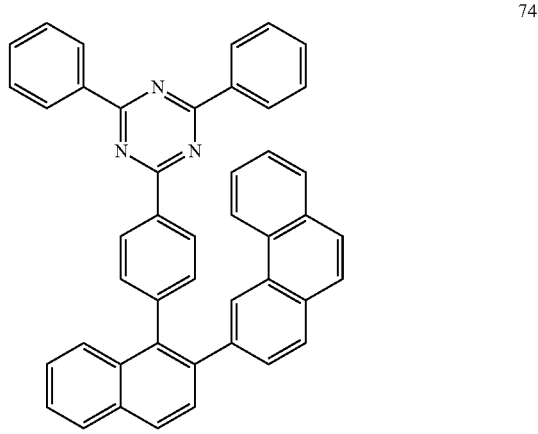

75
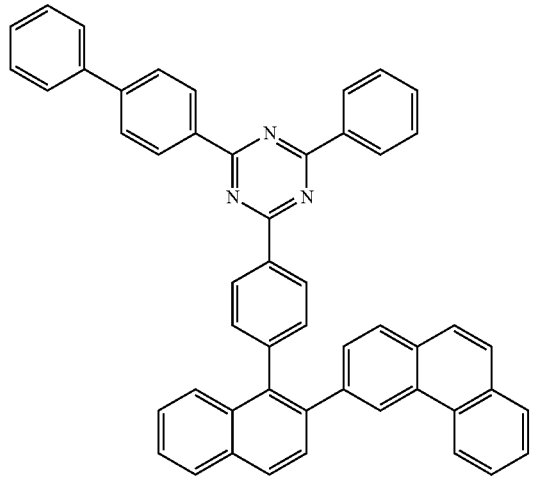
76
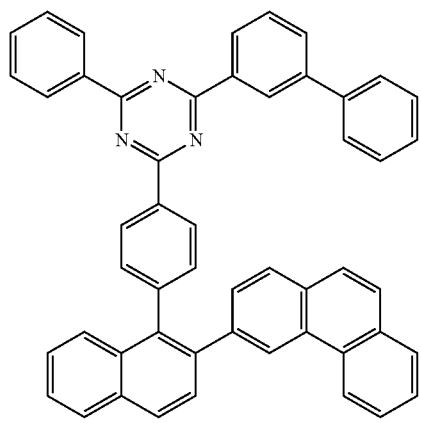
77
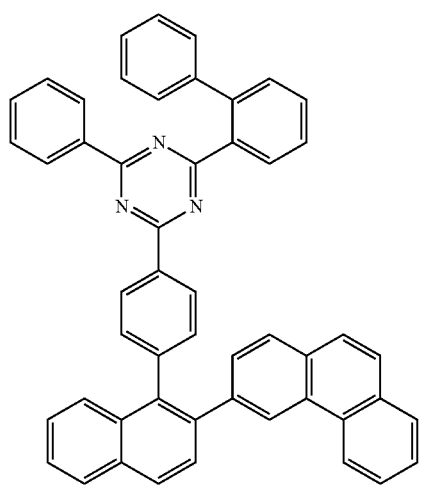
78
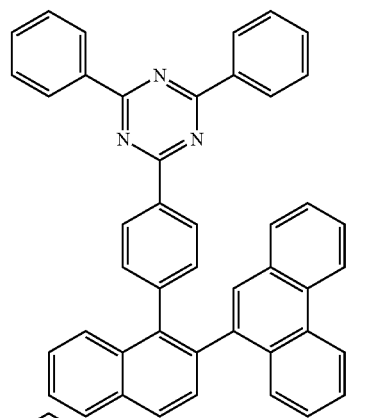
79
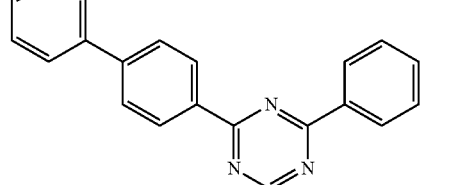
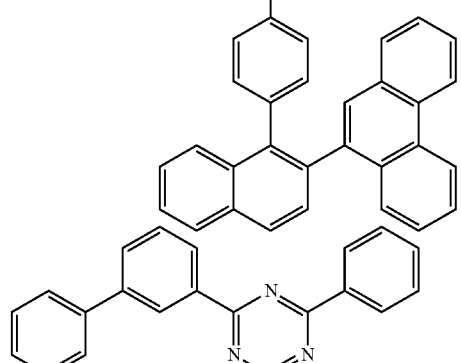
80
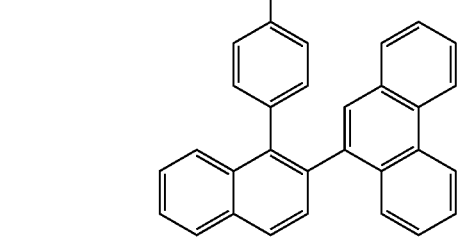
81
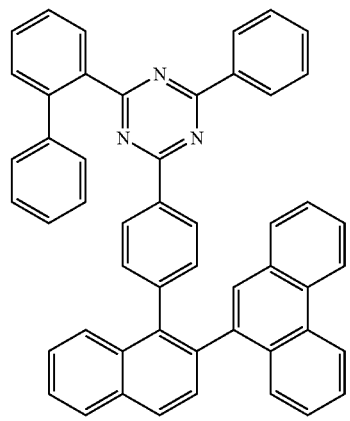

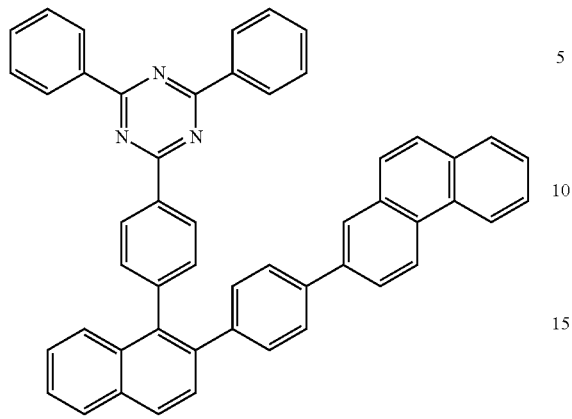
8. An organic light emitting device comprising: a first electrode; a second electrode provided to face the first electrode; and one or more organic material layers provided between the first electrode and the second electrode, wherein one or more of the organic material layers comprise the compound of claim 1.
* * * * *